United States Patent
Gallet et al.

(10) Patent No.: US 7,214,682 B2
(45) Date of Patent: *May 8, 2007

(54) SUBSTITUTED 2-PYRIDINYL-6,7,8,9-TETRAHYDROPYRIMIDO{1,2-A}PYRIMIDIN-4-ONE AND 7-PYRIDINYL-2,3-DIHYDROIMIDAZO{1,2-A}PYRIMIDIN-5(1H)ONE DERIVATIVES

(75) Inventors: Thierry Gallet, Palaiseau (FR); Patrick Lardenois, Bourg-la-Reine (FR); Alistair Lochead, Charenton le Pont (FR); Séverine Marguerie, Rennes (FR); Alain Nedelec, Colombes (FR); Mourad Saady, Paris (FR); Franck Slowinski, Thieux (FR); Philippe Yaiche, Les Lilas (FR)

(73) Assignees: Sanofi-aventis, Paris (FR); Mitsubishi Pharma Corporation, Osaka (JP)

(*) Notice: Subject to any disclaimer, the term of this patent is extended or adjusted under 35 U.S.C. 154(b) by 287 days.

This patent is subject to a terminal disclaimer.

(21) Appl. No.: 10/490,135

(22) PCT Filed: Sep. 19, 2002

(86) PCT No.: PCT/EP02/11128

§ 371 (c)(1),
(2), (4) Date: Sep. 7, 2004

(87) PCT Pub. No.: WO03/027116

PCT Pub. Date: Apr. 3, 2003

(65) Prior Publication Data

US 2005/0049261 A1    Mar. 3, 2005

(30) Foreign Application Priority Data

Sep. 21, 2001 (EP) .................. 01402432
Feb. 28, 2002 (EP) .................. 02290489

(51) Int. Cl.
| | |
|---|---|
| A01N 43/90 | (2006.01) |
| A61K 31/519 | (2006.01) |
| A01N 43/62 | (2006.01) |
| A61K 31/55 | (2006.01) |
| C07D 471/00 | (2006.01) |
| C07D 487/00 | (2006.01) |

(52) U.S. Cl. ............ 514/259.41; 514/221; 514/259.1; 544/279; 544/281

(58) Field of Classification Search ............ 544/279, 544/281; 514/221, 259.1, 259.41
See application file for complete search history.

(56) References Cited

U.S. PATENT DOCUMENTS 6,974,819 B2 * 12/2005 Garcia et al. .......... 514/259.41

FOREIGN PATENT DOCUMENTS

WO    WO 98/16528    4/1998

(Continued)

OTHER PUBLICATIONS

Leclerc, et al. ("Indirubins Inhibit Glycogen Synthase Kinase-3β and CDK5/P25, Two Protein Kinases Involved in Abnormal Tau Phosphorylation in Alzheimer's Disease," The Journal of Biological Chemistry, 276, No. 1, Jan. 2, 2001, pp. 251-260).*

(Continued)

*Primary Examiner*—Deepak Rao
*Assistant Examiner*—Cecilia Jaisle
(74) *Attorney, Agent, or Firm*—Balaram Gupta

(57) ABSTRACT

The invention relates to a pyrimidone derivative represented by formula (I) or a salt thereof wherein X represents two hydrogen atoms, a sulfur atom, an oxygen atom or a $C_{1-2}$ alkyl group and a hydrogen atom; Y represents a bond, an ethenylene group, an ethynylene group an oxygen atom, a sulfur atom, a sulfonyl group, a sulfoxide group, a carbonyl group, a hydroxyiminomethylene group, a dioxolan group, a nitrogen atom being optionally substituted; or a methylene group optionally substituted; or a methylene group optionally substituted; R1 represents a 2, 3 or 4-pyridine ring optionally substituted; R2 may represent a $C_{1-6}$ alkyl group optionally; a $C_{3-6}$ cycloalkyl group, a $C_{1-4}$ alkylthio group, a $C_{1-4}$ alkoxy group, a $C_{1-2}$ perhalogenated alkyl group, a $C_{1-3}$ halogenated alkyl group, a phenylthio group, a benzyl group, a benzene ring, an indan ring, a 5,6,7,8-tetrahydronaphthalene ring, a naphthalene ring, a pyridine ring, a pyrrole ring, a thiophene ring, a furan ring or an imidazole ring; R3 and R4 represent, each independently, a hydrogen atom, a $C_{1-6}$ alkyl group, a hydroxy group, a $C_{1-4}$ alkoxy group or a halogen atom; R5 represents a hydrogen atom, a $C_{1-6}$ alkyl group or a halogen atom; with the proviso that when R3 and R4 represent each a hydrogen atom then R5 is not a hydrogen atom. The invention relates also to a medicament comprising the said derivative or a salt thereof as an active ingredient which is used for preventive and/or therapeutic treatment of a neurodegenerative disease caused by abnormal activity of GSK3β or GSK3β, and cdk5/p25, such as Alzheimer disease (I)

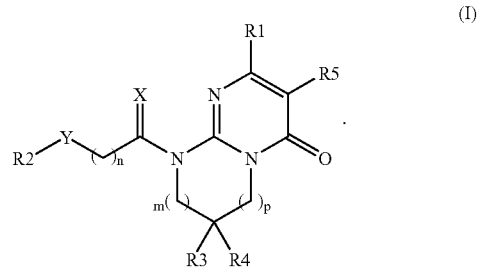

10 Claims, No Drawings

FOREIGN PATENT DOCUMENTS

| | | |
|---|---|---|
| WO | WO 98/24780 | 6/1998 |
| WO | WO 99/65897 | 12/1999 |
| WO | WO 00/18758 | 4/2000 |
| WO | WO 01/42224 | 6/2001 |
| WO | WO 01/44246 | 6/2001 |

OTHER PUBLICATIONS

Bhat, et al. ("Glycogen Synthase Kinase 3: A Drug Target for CNS Therapies," Journal of Neurochemistry, 2004, 89, 1313-1317).*

Souillac, et al., Characterization of Delivery Systems, Differential Scanning Calorimetry, pp. 217-221 (in Encyclopedia of Controlled Drug Delivery, 1999, John Wiley & Sons, pp. 212-227).*

Derivative (chemistry), retriieved from "http://en.wikipedia.org/wiki/Derivative-%28chemistry%29" on Aug. 10, 2006.*

List of neurodegenerative diseases; from the University of California, Nov. 2006.*

List of neurodegenerative diseases; from Wikipedia, Nov. 2006.*

Harwood, PubMed abstract of Curr. Mol. Med., Aug. 2003; 3(5): 472-82.*

* cited by examiner

SUBSTITUTED 2-PYRIDINYL-6,7,8,9-TETRAHYDROPYRIMIDO{1,2-A} PYRIMIDIN-4-ONE AND 7-PYRIDINYL-2,3-DIHYDROIMIDAZO {1,2-A}PYRIMIDIN-5(1H)ONE DERIVATIVES

TECHNICAL FIELD

The present invention relates to compounds that are useful as an active ingredient of a medicament for preventive and/or therapeutic treatment of neurodegenerative diseases caused by abnormal activities of GSK3β alone or by the combined effects of GSK3β and cdk5/p25.

BACKGROUND ART

GSK3β (glycogen synthase kinase 3β) is a proline directed serine, threonine kinase that plays an important role in the control of metabolism, differentiation and survival. It was initially identified as an enzyme able to phosphorylate and hence inhibit glycogen synthase. It was later recognized that GSK3β was identical to tau protein kinase 1 (TPK1), an enzyme that phosphorylates tau protein in epitopes that are also found to be hyperphosphorylated in Alzheimer's disease and in several tauopathies. Interestingly, protein kinase B (AKT) phosphorylation of GSK3β results in a loss of its kinase activity, and it has been hypothesized that this inhibition may mediate some of the effects of neurotrophic factors. Moreover, phosphorylation by GSK3β, of β-catenin, a protein involved in cell survival, results in its degradation by an ubiquitinilation dependent proteasome pathway. Thus, it appears that inhibition of GSK3β activity may result in neurotrophic activity. Indeed there is evidence that lithium, an non-competitive inhibitor of GSK3β, enhances neuritogenesis in some models and also increases neuronal survival, through the induction of survival factors such as Bcl-2 and the inhibition of the expression of proapoptotic factors such as P53 and Bax. Recent studies have demonstrated that β-amyloid increases the GSK3β activity and tau protein phosphorylation. Moreover, this hyperphosphorylation as well as the neurotoxic effects of β-amyloid are blocked by lithium chloride and by a GSK3β antisense mRNA. These observations strongly suggest that GSK3β may be the link between the two major pathological processes in Alzheimer's disease: abnormal APP (Amyloid Precursor Protein) processing and tau protein hyperphosphorylation.

Although tau hyperphosphorylation results in a destabilization of the neuronal cytoskeleton, the pathological consequences of abnormal GSK3β activity are, most likely, not only due to a pathological phosphorylation of tau protein because, as mentioned above, an excessive activity of this kinase may affect survival through the modulation of the expression of apoptotic and antiapoptotic factors. Moreover, it has been shown that β-amyloid-induced increase in GSK3β activity results in the phosphorylation and, hence the inhibition of pyruvate dehydrogenase, a pivotal enzyme in energy production and acetylcholine synthesis.

Cdk5/p25, also known as tau protein kinase 2 (TPK2), is a proline directed Ser/Thr kinase essential for central nervous system development and in particular for neuronal migration and neurite outgrowth. Cdk5 is a homologue of cyclin-dependent kinases and rather ubiquitously expressed. Its activator p35 (a 305 aa protein) or a truncated form p25 (208 aa, missing an N-terminal proline-rich domain not required for activity) are selectively expressed in neurons, limiting cdk5 kinase activity essentially to the CNS. Cdk5 is completely inactive in the absence of p35 or p25. The term cdk5/p25 will be used here for the active enzyme since evidence exists suggesting that p25 and less so p35 may be involved in pathological processes.

Physiological substrates of cdk5/p25 include DARPP-32, Munc-18, PAK1, synapsin 1 and perhaps some others. In addition, it is now well established that cdk5/p25 phosphorylates tau protein epitopes which are hyperphosphorylated in Alzheimer's disease. More recently, elevated cdk5/p25 activity, mislocalization of cdk5 and an increase in p25 activator has been found in the brain of Alzheimer patients. Interestingly, prephosphorylation of tau protein by cdk5/p25 considerably enhances phosphorylation of tau by GSK3β on other epitopes, also found hyperphosphorylated in Alzheimer's disease. Moreover, neurofibrillary tangles, the hallmark of Alzheimer's disease, are labeled with antisera for GSK3β and cdk5, but not GSK3α and MAP kinase, also, GSK3β and cdk5 are associated with microtubules and both, more than PKA and CK, contribute to the AD-like phosphorylation of tau protein. These results taken together suggest that mixed inhibitors of GSK3β and cdk5/p25 should efficient in protecting tau protein from hyperphosphorylation. Therefore, they would be useful in the treatment of any pathological disorder associated with the abnormal phosphorylation of tau protein, in particular Alzheimer's disease, but also other tauopathies (e.g. frontotemporoparietal dementia, corticobasal degeneration, Pick's disease, progressive supranuclear palsy).

Cdk5/p25 has been linked to apoptosis and neurodegeneration in more general terms. Its overexpression induces apoptosis in cultured neurons, in brain tissue apoptotic cells show strong immunoreactivity for cdk5. Neurotoxic agents, incl. Aβ(1–42), neuronal injury, ischemia or growth factor withdrawal lead to activation and mislocalization of cdk5/p25, abnormal phosphorylation of cdk5 substrates, cytoskeletal disruption and cell death. Moreover, phosphorylation by cdk5/p25 transforms DARPP-32 into an inhibitor of protein kinase A, reducing signal transduction in the striatum with obvious implications for Parkinson's disease. A role for cdk5 in ALS has also been proposed based on its ability to phosphorylate neurofilaments. More recently, deregulation of cdk5 was detected in a mouse model of amyotrophic lateral sclerosis.

Altogether, these experimental observations indicate that GSK3β inhibitors may find application in the treatment of the neuropathological consequences and the cognitive and attention deficits associated with Alzheimer's disease, as well as other acute and chronic neurodegenerative diseases. These include, in a non-limiting manner, Parkinson's disease, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma.

In addition GSK3β inhibition may find application in the treatment of other diseases such as:

Non-insulin dependent diabetes (such as diabetes type II) and obesity; manic depressive illness; schizophrenia; alopecia; cancers such as breast cancer, non-small cell lung carcinoma, thyroid cancer, T or B-cell leukemia and several virus-induced tumors.

Since it appears that both, GSK3β and cdk5/p25 play a major role in the induction of apoptosis in neuronal cells, combined inhibition of these two enzymes may find application in the treatment of not only Alzheimer's disease and the other above-mentioned tauopathies, but also in a number of other neurodegenerative disorders, in particular Parkinson's disease and amyotrophic lateral sclerosis; other dementias including vascular dementia; acute stroke and other traumatic injuries; cerebrovascular accidents (e.g. age related macular degeneration); brain and spinal cord trauma; peripheral neuropathies; retinopathies and glaucoma;

In addition mixed TPK1/TPK2 inhibitors may find their applications in the treatment of other diseases such as: smoking cessation and other withdrawal syndromes, epilepsy.

DISCLOSURE OF THE INVENTION

An object of the present invention is to provide compounds useful as an active ingredient of a medicament for preventive and/or therapeutic treatment of a disease caused by abnormal GSK3β or GSK3β and cdk5/p25 activity, more particularly of neurodegenerative diseases. More specifically, the object is to provide novel compounds useful as an active ingredient of a medicament that enables prevention and/or treatment of neurodegenerative diseases such as Alzheimer's disease.

Thus, the inventors of the present invention have identified compounds possessing inhibitory activity against GSK3β. As a result, they found that compounds represented by the following formula (I) had the desired activity and were useful as an active ingredient of a medicament for preventive and/or therapeutic treatment of the aforementioned diseases.

The present invention thus provides pyrimidone derivatives represented by formula (I) or salts thereof, solvates thereof or hydrates thereof:

wherein:

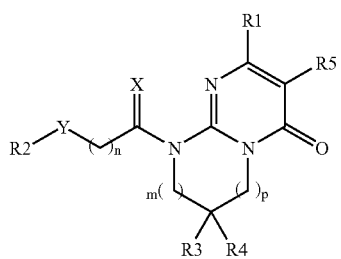

X represents two hydrogen atoms, a sulfur atom, an oxygen atom or a $C_{1-2}$ alkyl group and a hydrogen atom;

Y represents a bond, an ethenylene group, an ethynylene group, an oxygen atom, a sulfur atom, a sulfonyl group, a sulfoxide group, a carbonyl group, a hydroxyiminomethylene group, a dioxolan group, a nitrogen atom being optionally substituted by a $C_{1-6}$ alkyl group, a phenyl group or a benzyl group; or a methylene group optionally substituted by one or two groups chosen from a $C_{1-6}$ alkyl group, a benzyl group, a hydroxyl group, a $C_{1-4}$ alkoxy group, a $C_{1-2}$ perhalogenated alkyl group, an amino group, an acetylamino group or a phenyl group;

R1 represents a 2, 3 or 4-pyridine ring optionally substituted by a $C_{3-6}$ cycloalkyl group, a $C_{1-4}$ alkyl group, a $C_{1-4}$ alkoxy group, a benzyl group or a halogen atom;

when Y represents a bond, a methylene group optionally substituted, a hydroxyiminomethylene group, a dioxolan group or a carbonyl group then R2 represents a $C_{1-6}$ alkyl group optionally substituted by a hydroxy group, a $C_{6,10}$ aryloxy or a $C_{6,10}$ arylamino group; a $C_{3-6}$ cycloalkyl group, a $C_{1-4}$ alkylthio group, a $C_{1-4}$ alkoxy group, a $C_{1-2}$ perhalogenated alkyl group, a $C_{1-3}$ halogenated alkyl group, a phenylthio group, a benzyl group, a benzene ring, an indan ring, a 5,6,7,8-tetrahydronaphthalene ring, a naphthalene ring, a pyridine ring, a pyrrole ring, a thiophene ring, a furan ring or an imidazole ring; the benzyl group or the rings being optionally substituted by 1 to 4 substituents selected from a $C_{1-6}$ alkyl group, a methylendioxy group, a halogen atom, a $C_{1-2}$ perhalogenated alkyl group, a $C_{1-3}$ halogenated alkyl group, a hydroxyl group, a $C_{1-4}$ alkoxy group, a nitro, a cyano, an amino, a $C_{1-5}$ monoalkylamino group, a $C_{2-10}$ dialkylamino group, a $C_{1-6}$ alkylcarbonylamino group, a $C_{6,10}$ arylcarbonylamino group, a $C_{1-4}$ alkylsulfonyl group, $C_{1-4}$ alkylsulfonyloxy group or a phenyl group;

when Y represents a ethenylene group, a ethynylene group, an oxygen atom, a sulfur atom, a sulfonyl group, a sulfoxide group or a nitrogen atom being optionally substituted then R2 represents a $C_{1-6}$ alkyl group optionally substituted by a hydroxy group, a $C_{6,10}$ aryloxy or a $C_{6,10}$ arylamino group; a $C_{3-6}$ cycloalkyl group, a $C_{1-2}$ perhalogenated alkyl group, a $C_{1-3}$ halogenated alkyl group, a benzyl group, a benzene ring, an indan ring, a 5,6,7,8-tetrahydronaphthalene ring, a naphthalene ring, a $C_{6,10}$ arylamino, a pyridine ring, a pyrrole ring, a thiophene ring, a furan ring or an imidazole ring the benzyl group or the rings being optionally substituted by 1 to 4 substituents selected from a $C_{1-6}$ alkyl group, a methylendioxy group, a halogen atom, a $C_{1-2}$ perhalogenated alkyl group, a $C_{1-3}$ halogenated alkyl group, a hydroxyl group, a $C_{1-4}$ alkoxy group, a nitro, a cyano, an amino, a $C_{1-5}$ monoalkylamino group, a $C_{2-10}$ dialkylamino group, a $C_{1-6}$ alkylcarbonylamino group, a $C_{6-10}$ arylcarbonylamino group, a $C_{1-4}$ alkylsulfonyl group, $C_{1-4}$ alkylsulfonyloxy group or a phenyl group;

R3 represents a hydrogen atom, a $C_{1-6}$ alkyl group, a hydroxy group, a $C_{1-4}$ alkoxy group or a halogen atom;

R4 represents a hydrogen atom, a $C_{1-6}$ alkyl group, a hydroxy group, a $C_{1-4}$ alkoxy group or a halogen atom;

R5 represents a hydrogen atom, a $C_{1-6}$ alkyl group or a halogen atom; with the proviso that when R3 and R4 represent each a hydrogen atom then R5 is not a hydrogen atom;

When m equals 0, p equals 1, 2 or 3,
When m equals 1, p equals 0, 1 or 2,
When m equals 2, p equals 0 or 1; and
n represents 0 to 3.

According to another aspect of the present invention, there is provided a medicament comprising as an active ingredient a substance selected from the group consisting of the pyrimidone derivatives represented by formula (I) and the physiologically acceptable salts thereof, and the solvates thereof and the hydrates thereof. As preferred embodiments of the medicament, there are provided the aforementioned medicament which is used for preventive and/or therapeutic treatment of diseases caused by abnormal GSK3β or GSK3β and cdk5/p25 activity, and the aforementioned medicament which is used for preventive and/or therapeutic treatment of neurodegenerative diseases and in addition other diseases such as:

Non-insulin dependent diabetes (such as diabetes type II) and obesity; manic depressive illness; schizophrenia; alopecia; smoking cessation and other withdrawal syndromes, epilepsy; cancers such as breast cancer, non-small cell lung carcinoma, thyroid cancer, T or B-cell leukemia and several virus-induced tumors.

As further preferred embodiments of the present invention, there are provided the aforementioned medicament wherein the diseases are neurodegenerative diseases and are selected from the group consisting of Alzheimer's disease, Parkinson's disease, amyotrophic lateral sclerosis, tauopathies (e.g. frontotemporoparietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma, and the aforementioned medicament in the form of pharmaceutical composition containing the above substance as an active ingredient together with one or more pharmaceutical additives.

The present invention further provides an inhibitor of GSK3β or GSK3β and cdk5/p25 activity comprising as an active ingredient a substance selected from the group consisting of the pyrimidone derivatives of formula (I) and the salts thereof, and the solvates thereof and the hydrates thereof.

According to further aspects of the present invention, there is provided a method for preventive and/or therapeutic treatment of neurodegenerative diseases caused by abnormal GSK3β or GSK3β and cdk5/p25 activity, which comprises the step of administering to a patient a preventively and/or therapeutically effective amount of a substance selected from the group consisting of the pyrimidone derivatives of formula (1) and the physiologically acceptable salts thereof, and the solvates thereof and the hydrates thereof; and a use of a substance selected from the group consisting of the pyrimidone derivatives of formula (I) and the physiologically acceptable salts thereof, and the solvates thereof and the hydrates thereof for the manufacture of the aforementioned medicament.

As used herein, the $C_{1-6}$ alkyl group represents a straight or branched alkyl group having 1 to 6 carbon atoms, for example, methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, isohexyl group, and the like;

The $C_{1-4}$ alkoxy group represents an alkyloxy group having 1 to 4 carbon atoms for example, methoxy group, ethoxy group, propoxy group, isopropoxy group, butoxy group, isobutoxy group, sec-butoxy group, tert-butoxy group, and the like;

The halogen atom represents a fluorine, chlorine, bromine or iodine atom;

The $C_{1-2}$ perhalogenated alkyl group represents an alkyl group wherein all the hydrogen have been substituted by a halogeno, for example a $CF_3$ or $C_2F_5$;

The $C_{1-3}$ halogenated alkyl group represents an alkyl group wherein at least one hydrogen has not been substituted by a halogen atom;

The $C_{1-5}$ monoalkylamino group represents an amino group substituted by one $C_{1-5}$ alkyl group, for example, methylamino group, ethylamino group, propylamino group, isopropylamino group, butylamino group, isobutylamino group, tert-butylamino group, pentylamino group and isopentylamino group;

The $C_{2-10}$ dialkylamino group represents an amino group substituted by two $C_{1-5}$ alkyl groups, for example, dimethylamino group, ethylmethylamino group, diethylamino group, methylpropylamino group and diisopropylamino group;

The $C_{6,10}$ arylamino group represents an amino group substituted by a phenyl group or a naphthyl group;

The $C_{6,10}$ aryloxy group represents a phenyloxy group and a naphthyloxy group.

The dioxolan group represents the following group:

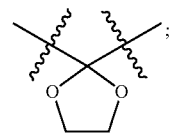

The hydroxyiminomethylene group represents the following group:

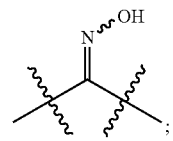

The ethenylene group represents the divalent group of formula:

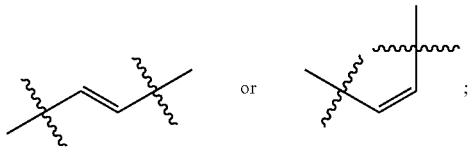

The ethynylene group represents the divalent group of formula:

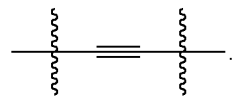

The leaving group represents a group which could be easily cleaved and substituted, such a group may be for example a tosyl, a mesyl, a bromide and the like.

The compounds represented by the aforementioned formula (I) may form a salt. Examples of the salt include, when an acidic group exists, salts of alkali metals and alkaline earth metals such as lithium, sodium, potassium, magnesium, and calcium; salts of ammonia and amines such as methylamine, dimethylamine, trimethylamine, dicyclohexylamine, tris(hydroxymethyl)-aminomethane, N,N-bis(hydroxyethyl)piperazine, 2-amino-2-methyl-1-propanol, ethanolamine, N-methylglucamine, and L-glucamine; or salts with basic amino acids such as lysine, δ-hydroxylysine, and arginine. The base-addition salts of acidic compounds are prepared by standard procedures well known in the art.

When a basic group exists, examples include salts with mineral acids such as hydrochloric acid, hydrobromic acid, sulfuric acid, nitric acid, phosphoric acid; salts with organic acids such as methanesulfonic acid, benzenesulfonic acid, p-toluenesulfonic acid, acetic acid, propionic acid, tartaric acid, fumaric acid, maleic acid, malic acid, oxalic acid, succinic acid, citric acid, benzoic acid, mandelic acid, cinnamic acid, lactic acid, glycolic acid, glucuronic acid, ascorbic acid, nicotinic acid, and salicylic acid; or salts with acidic amino acids such as aspartic acid, and glutamic acid.

The acid-addition salts of the basic compounds are prepared by standard procedures well know in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not compromised by side effects ascribable to the anions. Although medicinally acceptable salts of the basic compounds are preferred, all acid-addition salts are within the scope of the present invention.

In addition to the pyrimidone derivatives represented by the aforementioned formula (I) and salts thereof, their solvates and hydrates also fall within the scope of the present invention. The pyrimidone derivatives represented by the aforementioned formula (I) may have one or more asymmetric carbon atoms. As for the stereochemistry of such asymmetric carbon atoms, they may independently be in either (R) and (S) configuration, and the pyrimidone derivative may exist as stereoisomers such as optical isomers, or diastereoisomers. Any stereoisomers in pure form, any mixtures of stereoisomers, racemates and the like fall within the scope of the present invention.

Examples of preferred compounds of the present invention are shown in table 1 and table 2 hereinafter. However, the scope of the present invention is not limited by these compounds.

Preferred compounds of the present invention represented by formula (I) include also:
(1) Compounds wherein R1 represents a 3- or 4-pyridine ring and more preferably 4-pyridine ring, which may be substituted by a $C_{1-2}$ alkyl group, a $C_{1-2}$ alkoxy group or a halogen atom; and/or
(2) X represents two hydrogen atoms, an oxygen atom or a $C_{1-2}$ alkyl group and a hydrogen atom;
(3) Y represents a bond, a carbonyl group, a hydroxyiminomethylene group, a dioxolan group; or a methylene group optionally substituted by one or two groups chosen from a $C_{1-6}$ alkyl group, a benzyl group, a hydroxyl group, a $C_{1-4}$ alkoxy group, a $C_{1-2}$ perhalogenated alkyl group, an amino group, an acetylamino group or a phenyl group.

More preferred compounds of the present invention represented by formula (I) include also:
(1) Compounds wherein R1 represents an unsubstituted 4-pyridine ring;
Particularly preferred compounds of the present invention represented by formula (I) include compounds of table 1:
1. 9-[3-(2-Fluorophenyl)-propyl]-7,7-dimethyl-2-(pyridin-4-yl)-6,7,8,9-tetrahydro-4H-pyrimido[1,2-a]pyrimidin-4-one
2. 9-(2-Oxo-2-phenyl-ethyl)-7,7-dimethyl-2-(pyridin-4-yl)-6,7,8,9-tetrahydro-4H-pyrimido[1,2-a]pyrimidin-4-one
3. 9-(2-Hydroxy-2-phenyl-ethyl)-7,7-dimethyl-2-(pyridin-4-yl)-6,7,8,9-tetrahydro-4H-pyrimido[1,2-a]pyrimidin-4-one
4. 9-(2-Oxo-2-phenyl-ethyl)-7,7-difluoro-2-(pyridin-4-yl)-6,7,8,9-tetrahydro-4H-pyrimido[1,2-a]pyrimidin-4-one
5. 9-(2(S)-Hydroxy-2-phenyl-ethyl)-7,7-difluoro-2-(pyridin4-yl)-6,7,8,9-tetrahydro-4H-pyrimido[1,2-a]pyrimidin-4-one
6. 9-(2-Oxo-2-phenyl-ethyl)-3-fluoro-7,7-dimethyl-2-(pyridin-4-yl)-6,7,8,9-tetrahydro-4H-pyrimido[1,2-a]pyrimidin-4-one
7. 9-[2-Oxo-2-(3-chlorophenyl)-ethyl]-7,7-dimethyl-2-(pyridin-4-yl)-6,7,8,9-tetrahydro-4H-pyrimido[1,2-a]pyrimidin-4-one
8. 9-(2(S)-Hydroxy-2-phenyl-ethyl)-7,7-dimethyl-2-(pyridin-4-yl)-6,7,8,9-tetrahydro-4H-pyrimido[1,2-a]pyrimidin-4-one
9. 9-[2-Oxo-2-(3-fluorophenyl)-ethyl]-7,7-dimethyl-2-(pyridin-4-yl)-6,7,8,9-tetrahydro-4H-pyrimido[1,2-a]pyrimidin-4-one
10. 9-[2-Hydroxy-2-(3-chlorophenyl)-ethyl]-7,7-dimethyl-2-(pyridin-4-yl)-6,7,8,9-tetrahydro-4H-pyrimido[1,2-a]pyrimidin-4-one
11. 9-[2-Hydroxy-2-(3-fluorophenyl)-ethyl]-7,7-dimethyl-2-(pyridin-4-y)-6,7,8,9-tetrahydro-4H-pyrimido[1,2-a]pyrimidin-4-one
12. 9-(2(S)-Hydroxy-2-phenyl-ethyl)-3-fluoro-7,7-dimethyl-2-(pyridin-4-yl)-6,7,8,9-tetrahydro-4H-pyrimido[1,2-a]pyrimidin-4-one
13. 9-[2-Oxo-2-(4-fluorophenyl)-ethyl]-7,7-dimethyl-2-(pyridin-4-yl)-6,7,8,9-tetrahydro-4H-pyrimido[1,2-a]pyrimidin-4-one
14. 9-[2-Oxo-2-(5,5,8,8-tetramethyl-5,6,7,8-tetrahydronaphth-2-yl)-ethyl]-7,7-dimethyl-2-(pyridin-4-yl)-6,7,8,9-tetrahydro-4H-pyrimido[1,2-a]pyrimidin-4-one
15. 9-[2-Oxo-2-(3-methoxyphenyl)-ethyl]-7,7-dimethyl-2-(pyridin-4-yl)-6,7,8,9-tetrahydro-4H-pyrimido[1,2-a]pyrimidin-4-one
16. 9-[2-Oxo-2-(4-phenylphenyl)-ethyl]-7,7-dimethyl-2-(pyridin-4-yl)-6,7,8,9-tetrahydro-4H-pyrimido[1,2-a]pyrimidin-4-one
17. 9-[2-(1-Methyl-2-oxo-2-(3,4-methylendioxy-5-methoxyphenyl)-ethyl)]-7,7-dimethyl-2-(pyridin-4-yl)-6,7,8,9-tetrahydro-4H-pyrimido[1,2-a]pyrimidin-4-one
18. 9-[2-Oxo-2-(4-chlorophenyl)ethyl]-7,7-dimethyl-2-(pyridin-4-yl)-6,7,8,9-tetrahydro-4H-pyrimido[1,2-a]pyrimidin-4-one
19. 9-[2-Oxo-2-(naphth-2-yl)-ethyl]-7,7-dimethyl-2-(pyridin-4-yl)-6,7,8,9-tetrahydro-4H-pyrimido[1,2-a]pyrimidin-4-one
20. 9-[2-Oxo-2-(4-methylphenyl)-ethyl]-7,7-dimethyl-2-(pyridin-4-yl)-6,7,8,9-tetrahydro-4H-pyrimido[1,2-a]pyrimidin-4-one
21. 9-(2-Oxo-2-phenyl-ethyl)-7,7-dimethyl-3-bromo-2-(pyridin-4-yl)-6,7,8,9-tetrahydro-4H-pyrimido[1,2-a]pyrimidin-4-one
22. 9-(2(S)-Methoxy-2-phenyl-ethyl)-7,7-dimethyl-2-(pyridin-4-yl)-6,7,8,9-tetrahydro-4H-pyrimido[1,2-a]pyrimidin-4-one
23. 9-(3-Phenyl-propanoyl)-7,7-dimethyl-2-(pyridin-4-yl)-6,7,8,9-tetrahydro-4H-pyrimido[1,2-a]pyrimidin-4-one
24. 9-(2-Hydroxy-2-methyl-2-phenyl-ethyl)-7,7-dimethyl-2-(pyridin-4-yl)-6,7,8,9-tetrahydro-4H-pyrimido[1,2-a]pyrimidin-4-one
25. 9-(2-Methoxy-2-phenyl-2-trifluoromethyl-ethanoyl)-7,7-dimethyl-2-(pyridin-4-yl)-6,7,8,9-tetrahydro-4H-pyrimido[1,2-a]pyrimidin-4-one
26. 9-(2-Hydroxy-2,2-diphenylethyl)-7,7-dimethyl-2-(pyridin-4-yl)-6,7,8,9-tetrahydro-4H-pyrimido[1,2-a]pyrimidin-4-one
27. 9-(2-Hydroxyimino-2-phenyl-ethyl)-7,7-dimethyl-2-(pyridin-4-yl)-6,7,8,9-tetrahydro-4H-pyrimido[1,2-a]pyrimidin-4-one 28. 9-(2-Hydroxy-2-methyl-2-phenyl-ethyl)-7,7-dimethyl-3-fluoro-2-(pyridin-4-yl)-6,7,8,9-tetrahydro-4H-pyrimido[1,2-a]pyrimidin-4-one
29. 7,7-Dimethyl-9-(2-phenyl-[1,3]dioxolan-2-ylmethyl)-2-(pyridin-4-yl)-6,7,8,9-tetrahydro-4H-pyrimido[1,2-a]pyrimidin-4-one
30. 9-(2,3-Dihydroxypropyl)-7,7-dimethyl-2-(pyridin-4-yl)-6,7,8,9-tetrahydro-4H-pyrimido[1,2-a]pyrimidin-4-one
31. (2(R)-Methoxy-2-phenyl-ethyl)-7,7-dimethyl-2-(pyridin-4-yl)-6,7,8,9-tetrahydro-4H-pyrimido[1,2-a]pyrimidin-4-one
32. 9-(2-Hydroxy-3-phenylaminopropyl)-7,7-dimethyl-2-(pyridin-4-yl)-6,7,8,9-tetrahydro-4H-pyrimido[1,2-a]pyrimidin-4-one
33. 9-(2-Acetylamino-2-phenyl-ethyl)-7,7-dimethyl-2-(pyridin-4-yl)-6,7,8,9-tetrahydro-4H-pyrimido[1,2-a]pyrimidin-4-one
34. 9-(2-Amino-2-phenyl-ethyl)-7,7-dimethyl-2-(pyridin-4-yl)-6,7,8,9-tetrahydro-4H-pyrimido[1,2-a]pyrimidin-4-one
35. 9-(2-Hydroxy-3-phenoxypropyl)-7,7-dimethyl-2-(pyridin-4-yl)-6,7,8,9-tetrahydro-4H-pyrimido[1,2-a]pyrimidin-4-one
36. 9-(2-Oxo-2-phenyl-ethyl)-3-fluoro-2-(pyridin-4-yl)-6,7,8,9-tetrahydro-4H-pyrimido[1,2-a]pyrimidin-4-one
37. 9-[2-Oxo-2-(3-fluorophenyl)-ethyl]-3-fluoro-2-(pyridin-4-yl)-6,7,8,9-tetrahydro-4H-pyrimido[1,2-a]pyrimidin-4-one
38. 9-(2-Oxo-2-phenyl-ethyl)-3-methyl-2-(pyridin-4-yl)-6,7,8,9-tetrahydro-4H-pyrimido[1,2-a]pyrimidin-4-one
39. 9-(2-Oxo-2-phenyl-ethyl)-3-chloro-2-(pyridin-4-yl)-6,7,8,9-tetrahydro-4H-pyrimido[1,2-a]pyrimidin-4-one
40. 9-(2-Oxo-2-phenyl-ethyl)-3-bromo-2-(pyridin-4-yl)-6,7,8,9-tetrahydro-4H-pyrimido[1,2-a]pyrimidin-4-one
41. 2-(7-Methyl-6-oxo-8-pyridinyl-3,4-dihydro-2H,6H pyrimido[1,2-a]pyrimidin-1-yl)-N-phenyl-acetamide
42. 9-(2(S)-Hydroxy-2-phenyl-ethyl)-3-chloro-2-(pyridin-4-yl)-6,7,8,9-tetrahydro-4H-pyrimido[1,2-a]pyrimidin-4-one
43. 9-(2(S)-Hydroxy-2-phenyl-ethyl)-3-methyl-2-(pyridin-4-yl)-6,7,8,9-tetrahydro-4H-pyrimido[1,2-a]pyrimidin-4-one
44. 9-(2(S)-Hydroxy-2-phenyl-ethyl)-3-fluoro-2-(pyridin-4-yl)-6,7,8,9-tetrahydro-4H-pyrimido[1,2-a]pyrimidin-4-one
45. 9-(2(S)-Methoxy-2-phenyl-ethyl)-3-fluoro-2-(pyridin-4-yl)-6,7,8,9-tetrahydro-4H-pyrimido[1,2-a]pyrimidin-4-one
46. 9-(2(R)-Methoxy-2-phenyl-ethyl)-3-fluoro-2-(pyridin-4-yl)-6,7,8,9-tetrahydro-4H-pyrimido[1,2-a]pyrimidin-4-one
47. 9-[3-(2-Fluorophenyl)propyl]-7-hydroxy-2-(pyridin-4-yl)-6,7,8,9-tetrahydro-4H-pyrimido[1,2-a]pyrimidin-4-one
48. 9-[3-(2-Fluorophenyl)propyl]-7-methoxy-2-(pyridin-4-yl)-6,7,8,9-tetrahydro-4H-pyrimido[1,2-a]pyrimidin-4-one
49. 9-(2-Oxo-2-phenyl-ethyl)-7-methyl-2-(pyridin-4-yl)-6,7,8,9-tetrahydro-4H-pyrimido[1,2-a]pyrimidin-4-one
50. 9-(2-Hydroxy-2-phenyl-ethyl)-7-methyl-2-(pyridin-4-yl)-6,7,8,9-tetrahydro-4H-pyrimido[1,2-a]pyrimidin-4-one
51. 9-(2-Hydroxy-2-methyl-2-phenyl-ethyl)-7,7-dimethyl-2-(pyridin-4-yl)-6,7,8,9-tetrahydro-4H-pyrimido[1,2-a]pyrimidin-4-one
52. 9-(2-Hydroxy-2-methyl-2-phenyl-ethyl)-7,7-dimethyl-2-(pyridin-4-yl)-6,7,8,9-tetrahydro-4H-pyrimido[1,2-a]pyrimidin-4-one
53. 9-(2(R)-Methoxy-2-phenyl-ethyl)-7,7-dimethyl-2-(pyridin-4-yl)-6,7,8,9-tetrahydro-4H-pyrimido[1,2-a]pyrimidin-4-one
54. 3-Fluoro-9-[2-(4-fluoro-2-methoxy-phenyl)-ethyl]-2-(pyridin-4-yl)-6,7,8,9-tetrahydro-4H-pyrimido[1,2-a]pyrimidin-4-one
55. 9-Indan-2-ylmethyl-7,7-dimethyl-2-(pyridin-4-yl)-6,7,8,9-tetrahydro-4H-pyrimido[1,2-a]pyrimidin-4-one
56. 3-Fluoro-9-[2-(4-fluoro-2-methoxy-phenyl)-ethyl]-7,7-dimethyl-2-(pyridin-4-yl)-6,7,8,9-tetrahydro-4H-pyrimido[1,2-a]pyrimidin-4-one
57. 9-[2-(4-Fluoro-2-methoxy-phenyl)-ethyl]-7,7-dimethyl-2-(pyridin-4-yl)-6,7,8,9-tetrahydro-4H-pyrimido[1,2-a]pyrimidin-4-one;

and compounds of table 2:
1. [3-(2-Fluoro-phenyl)-propyl]-2,2-dimethyl-7-(pyridin-4-yl)-2,3-dihydro-1H-imidazo[1,2-a]pyrimidin-5-one
2. [2-Oxo-2-phenylethyl]-2,2-dimethyl-7-(pyridin-4-yl)-2,3-dihydro-1H-imidazo[1,2-a]pyrimidin-5-one
3. [2-Hydroxy-2-phenylethyl]-2,2-dimethyl-7-(pyridin-4-yl)-2,3-dihydro-1H-imidazo[1,2-a]pyrimidin-5-one
4. [2-Oxo-2-(4-chlorophenyl)ethyl]-2,2-dimethyl-7-(pyridin-4-yl)-2,3-dihydro-1H-imidazo[1,2-a]pyrimidin-5-one
5. [2-Oxo-2-(4-methylphenyl)ethyl]-2,2-dimethyl-7-(pyridin-4-yl)-2,3-dihydro-1H-imidazo[1,2-a]pyrimidin-5-one
6. [2-Oxo-4-phenylphenyl]-2,2-dimethyl-7-(pyridin-4-yl)-2,3-dihydro-1H-imidazo[1,2-a]pyrimidin-5-one
7. [1-Methyl-2-oxo-2-(3,4-methylendioxy-5-methoxyphenyl)-ethyl]-2,2-dimethyl-7-(pyridin-4-yl)-2,3-dihydro-1H-imidazo[1,2-a]pyrimidin-5-one
8. [2-Oxo-2-(naphth-2-yl)-ethyl]-2,2-dimethyl-7-(pyridin-4-yl)-2,3-dihydro-1H-imidazo[1,2-a]pyrimidin-5-one
9. [2-Oxo-2-(4-fluorophenyl)-ethyl]-2,2-dimethyl-7-(pyridin-4-yl)-2,3-dihydro-1H-imidazo[1,2-a]pyrimidin-5-one
10. [2-Oxo-2-(3-methoxyphenyl)-ethyl]-2,2-dimethyl-7-(pyridin-4-yl)-2,3-dihydro-1H-imidazo[1,2-a]pyrimidin-5-one
11. [2-Oxo-2-(5,5,8,8-tetramethyl-5,6,7,8-tetrahydronaphth-2-yl)-ethyl]-2,2-dimethyl-7-(pyridin-4-yl)-2,3-dihydro-1H-imidazo[1,2-a]pyrimidin-5-one;

and compounds of table 3:
1. 9-[2-(4-Fluoro-2-methoxy-phenyl)-ethyl]-8-methyl-2-(pyridin-4-yl)6,7,8,9-tetrahydro-pyrimido[1,2-a]pyrimidin-4-one
2. 9-[2-(4-Fluoro-2-methoxy-phenyl)-ethyl]-8,8-dimethyl-2-(pyridin8-4-y)-6,7,8,9-tetrahydro-pyrimido[1,2-a]pyrimidin-4-one
3. 9-[2-(4-Fluoro-phenyl)-ethyl]-8-methyl-2-(pyridin-4-yl)-6,7,8,9-tetrahydro-pyrimido[1,2-a]pyrimidin-4-one
4. 8-Methyl-9-(2-oxo-2-phenyl-ethyl)-2-(pyridin-4-yl)-6,7,8,9-tetrahydro-pyrimido[1,2-a]pyrimidin-4-one
5. 9-[2-(2,5-Dimethoxy-phenyl)-ethyl]-8-methyl-2-(pyridin-4-yl)-6,7,8,9-tetrahydro-pyrimido[1,2-a]pyrimidin-4-one
6. 9-[2-(2-methoxy-phenyl)-ethyl]-8-methyl-2-(pyridin-4-yl)-6,7,8,9-tetrahydro-pyrimido[1,2-a]pyrimidin-4-one.
7. 9-[2(S)-Hydroxy-2-phenyl-ethyl]-8-methyl-2-(pyridin-4-yl)-6,7,8,9-tetrahydro-pyrimido[1,2-a]pyrimidin-4-one
8. 9-[2(S)-Hydroxy-2-phenyl-ethyl]-8,8-dimethyl-2-(pyridin-4-yl)-6,7,8,9-tetrahydro-pyrimido[1,2-a]pyrimidin-4-one
9. 8-Methyl-9-[naphthalen-1-ylmethyl]-2-(pyridin-4-yl)-6,7,8,9-tetrahydro-pyrimido[1,2-a]pyrimidin-4-one 10. 8,8-Dimethyl-9-[2-oxo-2-phenyl-ethyl]-2(pyridin-4-yl)-6,7,8,9-tetrahydro-pyrimido[1,2-a]pyrimidin-4-one
11. 8-Methyl-9-[naphthalen-2-ylmethyl]-2-(pyridin-4-yl)-6,7,8,9-tetrahydro-pyrimido[1,2-a]pyrimidin-4-one
12. 9-[2-(3-Methoxy-phenyl)-2-oxo-ethyl]-8-methyl-2-(pyridin-4-yl)-6,7,8,9-tetrahydro-pyrimido[1,2-a]pyrimidin-4-one
13. 9-[2-(3-Chloro-phenyl)-2-oxo-ethyl]-8-methyl-2-(pyridin-4-yl)-6,7,8,9-tetrahydro-pyrimido[1,2-a]pyrimidin-4-one
14. 8,8-Dimethyl-9-[2(S)-phenyl-propyl]-2-(pyridin-4-yl)-6,7,8,9-tetrahydro-pyrimido[1,2-a]pyrimidin-4-one
15. 8,8-Dimethyl-9-[2(R)-phenyl-propyl]-2-(pyridin-4-yl)-6,7,8,9-tetrahydro-pyrimido[1,2-a]pyrimidin-4-one
16. 8-Ethyl-9-[2-oxo-2-phenyl-ethyl]-2-(pyridin-4-yl)-6,7,8,9-tetrahydro-pyrimido[1,2-a]pyrimidin-4-one
17. 8-Ethyl-9-[2(S)-hydroxy-2-phenyl-ethyl]-2-(pyridin-4-yl)-6,7,8,9-tetrahydro-pyrimido[1,2-a]pyrimidin-4-one
18. 3-Fluoro-8-methyl-9-(2-oxo-2-phenyl-ethyl)-2-(pyridin-4-yl)-6,7,8,9-tetrahydro-pyrimido[1,2-a]pyrimidin-4-one
19. 8,8-Dimethyl-9[naphthalen-1-ylmethyl]-2-(pyridin-4-yl)-6,7,8,9-tetrahydro-pyrimido[1,2-a]pyrimidin-4-one
20. 9-[2-(4-Fluoro-phenyl)-2(S)-hydroxy-ethyl]-8,8-dimethyl-2-(pyridin-4-yl)-6,7,8,9-tetrahydro-pyrimido[1,2-a]pyrimidin-4-one
21. 9-[2-(3-Fluoro-phenyl)-2-hydroxy-ethyl]-8-methyl-2-(pyridin-4-yl)-6,7,8,9-tetrahydro-pyrimido[1,2-a]pyrimidin-4-one
22. 9-[2-(3,5-Dichloro-phenyl)-2-hydroxy-ethyl]-8-methyl-2-(pyridin-4-yl)-6,7,8,9-tetrahydro-pyrimido[1,2-a]pyrimidin-4-one
23. 9-[2-Benzo[1,3]dioxol-5-yl-2-oxo-ethyl]-8-methyl-2-(pyridin-4-yl)-6,7,8,9-tetrahydro-pyrimido[1,2-a]pyrimidin-4-one
24. 9-[2-(3-Bromo-phenyl)-2(S)-hydroxy-ethyl]-8,8-dimethyl-2-(pyridin-4-yl)-6,7,8,9-tetrahydro-pyrimido[1,2-a]pyrimidin-4-one
25. 9-[2-(2,3-Dihydro-benzo[1,4]dioxin-6-yl)-2-oxo-ethyl]-8-methyl-2-(pyridin-4-yl)-6,7,8,9-tetrahydro-pyrimido[1,2-a]pyrimidin-4-one
26. 3-Fluoro-9-(2-(S)-hydroxy-2-phenyl-ethyl)-8-methyl-2-(pyridin-4-yl)-6,7,8,9-tetrahydro-pyrimido[1,2-a]pyrimidin-4-one
27. 9-(2-Biphenyl-4-yl-2(S)-hydroxy-ethyl)-8,8-dimethyl-2-(pyridin-4-yl)-6,7,8,9-tetrahydro-pyrimido[1,2-a]pyrimidin-4-one
28. 9-[2-(3-Fluoro-phenyl)-2(S)-hydroxy-ethyl]-8,8-dimethyl-2-(pyridin-4-yl)-6,7,8,9-tetrahydro-pyrimido[1,2-a]pyrimidin-4-one
29. 9-(2(S)-Hydroxy-2-naphthalen-2-yl-ethyl)-8,8-dimethyl-2-(pyridin-4-yl)-6,7,8,9-tetrahydro-pyrimido[1,2-a]pyrimidin-4-one
30. 9-[2-(4-Chloro-phenyl)-2(S)-hydroxy-ethyl]-8,8-dimethyl-2-(pyridin-4-yl)-6,7,8,9-tetrahydro-pyrimido[1,2-a]pyrimidin-4-one
31. 9-[2-(3,4-Dichlorophenyl)-2(S)-hydroxy-ethyl]-8,8-dimethyl-2-(pyridin-4-yl)-6,7,8,9-tetrahydro-pyrimido[1,2-a]pyrimidin-4-one
32. 9-(2(S)-Hydroxy-2-p-tolyl-ethyl)-8,8-dimethyl-2-(pyridin-4-yl)-6,7,8,9-tetrahydro-pyrimido[1,2-a]pyrimidin-4-one
33. 3-Bromo-8-methyl-9-(2-oxo-2-phenyl-ethyl)-2-pyridin-4-yl-6,7,8,9-tetrahydro-pyrimido[1,2-a]pyrimidin-4-one
34. 9-[2(S)-Hydroxy-2-(3-methoxy-phenyl)-ethyl]-8,8-dimethyl-2-(pyridin-4-yl)-6,7,8,9-tetrahydro-pyrimido[1,2-a]pyrimidin-4-one
35. 9-[2-(2,4-Dichloro-phenyl)-2(S)-hydroxy-ethyl]-8,8-dimethyl-2-(pyridin-4-yl)-6,7,8,9-tetrahydro-pyrimido[1,2-a]pyrimidin-4-one
36. 3-Fluoro-9-(2(S)-hydroxy-2-phenyl-ethyl)-8,8-dimethyl-2-(pyridin-4-yl)-6,7,8,9-tetrahydro-pyrimido[1,2-a]pyrimidin-4-one;
37. 9-[2-(3-Methoxy-phenyl)-2oxo-ethyl]-8,8-dimethyl-2-pyridin-4-yl-6,7,8,9-tetrahydro-pyrimido[1,2-a]pyrimidin-4-one;
38. 9-[2(S)-Hydroxy-2-phenyl-ethyl]-8-methyl-2-(pyridin-4-yl)-6,7,8,9-tetrahydro-pyrimido[1,2-a]pyrimidin-4-one (diastereoisomer I);
39. 9-[2(S)-Hydroxy-2-phenyl-ethyl]-8-methyl-2-(pyridin-4-yl)6,7,8,9-tetrahydro-pyrimido[1,2-a]pyrimidin-4-one (diastereoisomer II);
40. 8,8-dimethyl 9-(2-oxo-2-p-tolyl-ethyl)-ethyl)-2-pyridin-4-yl-6,7,8,9-tetrahydro-pyrimido[1,2-a]pyrimidin-4-one;
41. 9-[2-(3-Bromo-phenyl)-2-oxo-ethyl]-8,8-dimethyl-2-pyridin-4-yl-6,7,8,9-tetrahydro-pyrimido[1,2-a]pyrimidin-4-one;
42. 4-[2-(2,2-Dimethyl-6-oxo-8-pyridin-4-yl-3,4-dihydro-2H,6H-pyrimido[1,2-a]pyrimidin-1-yl)-1-hydroxy-ethyl]-benzonitrile;
43. 9-[2-(3-Fluoro-phenyl)-2-oxo-ethyl]-8,8-dimethyl-2-pyridin-4-yl-6,7,8,9-tetrahydro-pyrimido[1,2-a]pyrimidin-4-one;
44. 9-[2-(3,4-Dichloro-phenyl)-2-hydroxy-ethyl]-8,8-dimethyl-2-pyridin-4-yl-6,7,8,9-tetrahydro-pyrimido[1,2-a]pyrimidin-4-one;
45. 9-[2-(4-Chloro-phenyl)-2-hydroxy-ethyl]-8-ethyl-2-pyridin-4-yl-6,7,8,9-tetrahydro-pyrimido[1,2-a]pyrimidin-4-one;
46. 9-[2-(3-Bromo-phenyl)-2-oxo-ethyl]-8-ethyl-2-pyridin-4-yl-6,7,8,9-tetrahydro-pyrimido[1,2-a]pyrimidin-4-one;
47. 9-[2-(4-chloro-phenyl)-2-oxo-ethyl]-8-ethyl-2-pyridin-4-yl-6,7,8,9-tetrahydro-pyrimido[1,2-a]pyrimidin-4-one;
48. 8-Ethyl-9-(2-hydroxy-2-p-tolyl-ethyl)-2-pyridin-4-yl-6,7,8,9-tetrahydro-pyrimido[1,2-a]pyrimidin-4-one.

As a further object, the present invention concerns also methods for preparing the compounds represented by the aforementioned formula (I).

These compounds can be prepared, for example, according to methods explained below.

Preparation Method

Pyrimidone compounds represented by the aforementioned formula (I) may be prepared according to scheme 1.

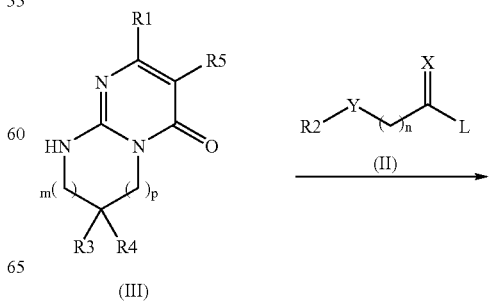

Scheme 1

-continued

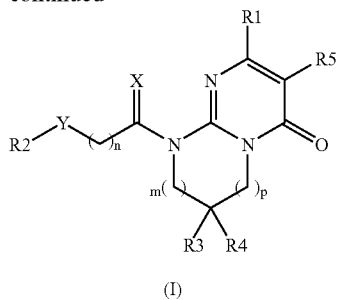

(I)

(In the above scheme the definition of R1, R2, R3, R4, R5, X, p, m and n are the same as those already described for compound of formula (I)).

The pyrimidone derivative represented by the above formula (III), wherein R1 is as defined for compound of formula (I), is allowed to react with a base such as sodium hydride, sodium carbonate or potassium carbonate in a solvent such as N,N-dimethylformamide, N-methylpyrrolidone, N,N-dimethylacetamide or chloroform at a suitable temperature ranging from 0 to 130° C. under ordinary air, then with a compound of formula (II), wherein R2, X, Y and n are as defined for compound of formula (I) and L represents a leaving group preferably bromide or mesyl group, is added to obtain the compound of the aforementioned formula (I).

Compound of formula (II) are commercially available or may be synthesized according to well-known methods of one skilled in the art. The compound of formula (III) may be prepared according to the method defined in scheme 2.

Scheme 2

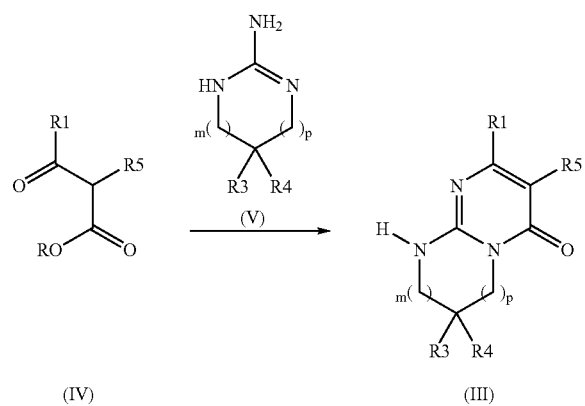

(In the above scheme the definition of R1, R3, R4, R5, p and m are the same as already described.)

According to this method, the 3-ketoester of formula (IV) is allowed to react with a compound of formula (V). The reaction may be carried out in the presence of potassium carbonate, in an alcoholic solvent such as methanol, ethanol and the like or without, at a suitable temperature ranging from 250°–1400° C. under ordinary air.

Alternatively, compounds of formula (III) wherein R5 represents a hydrogen atom may be halogenated in order to give compounds of formula (III) wherein R5 is an halogen atom such as a bromine atom or a chlorine atom. The reaction may be carried out in an acidic medium such as acetic acid or propionic acid, in presence of bromosuccinimide or chlorosuccinimide, or bromine.

In addition, compounds of formula (III) wherein R5 represents a fluorine atom may be obtained by analogy to the method described in Tetrahedron Letters, Vol.30, N°45, pp 6113–6116, 1989.

Compounds of formula (V) or (IV) are commercially available or may be synthesized according to well-known methods of one skilled in the art.

For example compounds of formula (IV), wherein R1 represent a pyridine ring optionally substituted by a $C_{1-4}$ alkyl group, $C_{1-4}$ alkoxy group or a halogen atom, can be prepared by reacting a nicotinic acid optionally substituted by a $C_{1-4}$ alkyl group, $C_{1-4}$ alkoxy group or an halogen, with a malonic acid monoester. The reaction can be carried out using methods well known to one skilled in the art, such as for example in presence of a coupling agent such as 1,1'-carbonylbis-1H-imidazole in a solvent such as tetrahydrofuran at a temperature ranging from 20 to 70° C.

Compounds of formula (I) may also be obtained starting from another compound of formula (I) using well-known methods of one skilled in the art.

In the above reactions, protection or deprotection of a functional group may sometimes be necessary. A suitable protecting group Pg can be chosen depending on the type of the functional group, and a method described in the literature may be applied. Examples of protecting group, of protection and deprotection methods are given for example in Protective groups in Organic Synthesis Greene et al., 2nd Ed. (John Wiley & Sons, Inc., New York).

The compounds of the present invention have inhibitory activity against GSK3β. Accordingly, the compounds of the present invention are useful as an active ingredient for the preparation of a medicament, which enables preventive and/or therapeutic treatment of a disease caused by abnormal GSK3β or GSK3β and cdk5/p25 activity and more particularly of neurodegenerative diseases such as Alzheimer's disease. In addition, the compounds of the present invention are also useful as an active ingredient for the preparation of a medicament for preventive and/or therapeutic treatment of neurodegenerative diseases such as Parkinson's disease, amyotrophic lateral sclerosis, tauopathies (e.g. frontotemporopadietal dementia, corticobasal degeneration, Pick's disease, progressive supranuclear palsy) and other dementia including vascular dementia; acute stroke and others traumatic injuries; cerebrovascular accidents (e.g. age related macular degeneration); brain and spinal cord trauma; peripheral neuropathies; retinopathies and glaucoma; and other diseases such as non-insulin dependent diabetes (such as diabetes type II) and obesity; manic depressive illness; schizophrenia; alopecia; smoking cessation and other withdrawal syndromes, epilepsy; cancers such as breast cancer, non-small cell lung carcinoma, thyroid cancer, T or B-cell leukemia and several virus-induced tumors.

The present invention further relates to a method for treating neurodegenerative diseases caused by abnormal activity of GSK3β or GSK3β and cdk5/p25 and of the aforementioned diseases which comprises administering to a mammalian organism in need thereof an effective amount of a compound of the formula (I).

As the active ingredient of the medicament of the present invention, a substance may be used which is selected from the group consisting of the compound represented by the aforementioned formula (I) and pharmacologically acceptable salts thereof, and solvates thereof and hydrates thereof. The substance, per se, may be administered as the medicament of the present invention, however, it is desirable to administer the medicament in a form of a pharmaceutical composition which comprises the aforementioned substance as an active ingredient and one or more pharmaceutical additives. As the active ingredient of the medicament of the present invention, two or more of the aforementioned substances may be used in combination. The above pharmaceutical composition may be supplemented with an active ingredient of another medicament for the treatment of the above mentioned diseases. The type of pharmaceutical composition is not particularly limited, and the composition may be provided as any formulation for oral or parenteral administration. For example, the pharmaceutical composition may be formulated, for example, in the form of pharmaceutical compositions for oral administration such as granules, fine granules, powders, hard capsules, soft capsules, syrups, emulsions, suspensions, solutions and the like, or in the form of pharmaceutical compositions for parenteral administrations such as injections for intravenous, intramuscular, or subcutaneous administration, drip infusions, transdermal preparations, transmucosal preparations, nasal drops, inhalants, suppositories and the like. Injections or drip infusions may be prepared as powdery preparations such as in the form of lyophilized preparations, and may be used by dissolving just before use in an appropriate aqueous medium such as physiological saline. Sustained-release preparations such as those coated with a polymer may be directly administered intracerebrally.

Types of pharmaceutical additives used for the manufacture of the pharmaceutical composition, content ratios of the pharmaceutical additives relative to the active ingredient, and methods for preparing the pharmaceutical composition may be appropriately chosen by those skilled in the art. Inorganic or organic substances, or solid or liquid substances may be used as pharmaceutical additives. Generally, the pharmaceutical additives may be incorporated in a ratio ranging from 1% by weight to 90% by weight based on the weight of an active ingredient.

Examples of excipients used for the preparation of solid pharmaceutical compositions include, for example, lactose, sucrose, starch, talc, cellulose, dextrin, kaolin, calcium carbonate and the like. For the preparation of liquid compositions for oral administration, a conventional inert diluent such as water or a vegetable oil may be used. The liquid composition may contain, in addition to the inert diluent, auxiliaries such as moistening agents, suspension aids, sweeteners, aromatics, colorants, and preservatives. The liquid composition may be filled in capsules made of an absorbable material such as gelatin. Examples of solvents or suspension mediums used for the preparation of compositions for parenteral administration, e.g. injections, suppositories, include water, propylene glycol, polyethylene glycol, benzyl alcohol, ethyl oleate, lecithin and the like. Examples of base materials used for suppositories include, for example, cacao butter, emulsified cacao butter, lauric lipid, witepsol.

The dose and frequency of administration of the medicament of the present invention are not particularly limited, and they may be appropriately chosen depending on conditions such as a purpose of preventive and/or therapeutic treatment, a type of a disease, the body weight or age of a patient, severity of a disease and the like. Generally, a daily dose for oral administration to an adult may be 0.01 to 1,000 mg (the weight of an active ingredient), and the dose may be administered once a day or several times a day as divided portions, or once in several days. When the medicament is used as an injection, administrations may preferably be performed continuously or intermittently in a daily dose of 0.001 to 100 mg (the weight of an active ingredient) to an adult.

CHEMICAL EXAMPLES

The present invention will be explained more specifically with reference to the following general examples, however, the scope of the present invention is not limited to these examples.

Example 1

Compound N° 8 of Table 1

9-(2(S)-Hydroxy-2-phenyl-ethyl)-7,7-dimethyl-2-(pyridin-4-yl)-6,7,8,9-tetrahydro-4H-pyrimido[1,2-a]pyrimidin-4-one hydrochloride (1:1)

1.1 7,7-dimethyl-2-(pyridin-4-yl)-6,7,8,9-tetrahydro-4H-pyrimido[1,2-a]pyrimidin-4-one A mixture of 5.9 g (30.55 mmol) of ethyl 3-(pyridin-4-yl)-3-oxopropionate, 5.0 g (30.55 mmol) of 5,5-dimethyl-1,4,5,6-tetrahydro-2-pyrimidinamine monohydrochloride (prepared by analogy to the method described in U.S. Pat. No. 4,262,122) and 6.33 g (45.82 mmol) of potassium carbonate in 60 ml of ethanol was heated at reflux temperature during 12 h. The cooled suspension was filtered and the solvent removed by evaporation. The residue obtained was dissolved in dichloromethane and washed with water. The organic phase was dried and evaporated to give 6.30 g (80%) of product as a beige solid. Mp.: 152–154° C.

1.2. 9-(2(S)-Hydroxy-2-phenyl-ethyl)-7,7-dimethyl-2-(pyridin-4-yl)-6,7,8,9-tetrahydro-4H-pyrimido[1,2-a]pyrimidin-4-one hydrochloride (1:1)

A suspension of 0.8 g (3.12 mmol) of 7,7-dimethyl-2-(pyridin-4-yl)-6,7,8,9-tetrahydro-4H-pyrimido[1,2-a]pyrimidin-4-one in 8 ml of anhydrous dimethylformamide was treated with 274 mg (6.86 mmol) of sodium hydride (60% suspension in mineral oil) and the resulting mixture was heated at 50° C. for 30 min. 0.494 ml (3.74 mmol) of (S)-2-chloro-1-phenylethanol was added and the reaction mixture was heated at 50° C. during 4 h.

The cooled solution was treated with water and extracted with ethyl acetate. The organic phase was dried and evaporated to give crude product, which was purified by silica gel chromatography, eluting with dichloromethane/methanol in the proportions 98/2 to 90/10. The 0.486 g of pure product obtained in the form of free base was dissolved in hot ethanol and treated with 1 equivalent of hydrogen-chloride in isopropanol. The cooled solution was filtered to afford 0.192 g (15%) of white solid. Mp: 234–236° C. $[\alpha]_D = -22.9°$ (c=1, $CH_3OH$)

Example 2

Compound N°49 of Table 1

9-(2-Oxo-2-phenyl-ethyl)-7-methyl-2-(pyridin-4-yl)-6,7,8,9-tetrahydro 4H-pyrimido[1,2-a]pyrimidin-4-one 2.1 5-Methyl-1,4,5,6-tetrahydro-2-pyrimidinamine hydrochloride To a solution containing 6.7 g (41.6 mmol) of 2-methyl-1,3-propandiamine hydrochloride (Tetrahedron (1994) 50(29), 8617–8632) in 50 ml of methanol was added 83 ml of a solution of sodium methylate in methanol (1 mmol/ml) and the resulting mixture treated with 3.97 g (41.6 mmol) of guanidine hydrochloride. The reaction mixture was heated at 140° C. for 3 h.

The solution was filtered, the solvent evaporated and the residue obtained was used directly in the next step.

2.2 7-Methyl-2-(pyridin-4-yl)-6,7,8,9-tetrahydro-4H-pyrimido[1,2-a]pyrimidin-4-one The product was obtained by analogy with step N° 1.1 and using the intermediate from step N° 2.1.

2.3 9-(2-Oxo-2-phenyl-ethyl)-7-methyl-2-(pyridin-4-yl)-6,7,8,9-tetrahydro 4H-pyrimido[1,2-a]pyrimidin-4-one A suspension of 0.32 g (1.34 mmol) of 7-methyl-2-(pyridin-4-yl)-6,7,8,9-tetrahydro-4H-pyrimido[1,2-a]pyrimidin-4-one in 10 ml of anhydrous dimethylformamide was treated with 64 mg (1.34 mmol) of sodium hydride (50% suspension in mineral oil) and the resulting mixture was stirred for 40 min. 0.267 g (1.34 mmol) of phenacyl bromide was added and the reaction mixture stirred at room temperature for 2 h.

The solution was treated with water and extracted with ethyl acetate. The organic phase was dried and evaporated to give crude product, which was purified by silica gel chromatography, eluting with dichloromethane/methanol in the proportions 100/0 to 90/10 to give 0.235 g of pure product obtained in the form of free base. Mp: 202–203° C.

Example 3

Compound N° 47 of Table 1

9-[3-(2-Fluorophenyl)propyl]-7-hydroxy-2-(pyridin-4-yl)-6,7,8,9-tetrahydro 4H-pyrimido[1,2-a]pyrimidin-4-one

3.1 7-Hydroxy-2-(pyridin-4-yl)-6,7,8,9-tetrahydro-4H-pyrimido[1,2-a]pyrimidin-4-one The product was obtained by analogy with step N° 1.1 and using 2-amino-1,4,5,6-tetrahydro-5-pyrimidinol (Arch.int. Pharmacodyn.Ther. (1968),175(1), 193–211). Mp.: 305–307° C.

3.2 9-[3-(2-Fluorophenyl)propyl]-7-hydroxy-2-(pyridin-4-yl)-6,7,8,9-tetrahydro 4H-pyrimido[1,2-a] pyrimidin-4-one A suspension of 1.0 g (4.09 mmol) of 7-hydroxy-2-(pyridin-4-yl)-6,7,8,9-tetrahydro-4H-pyrimido[1,2-a]pyrimidin-4-one and 0.95 g (4.09 mmol) of 1-[3-(methylsulfonyloxy)propyl]-2-fluorobenzene in 100 ml of anhydrous acetonitrile was treated with 4.1 g (1.42 mmol) of potassium fluoride suspended on alumina (Fluka) and the resulting mixture was heated at 80° C. for 24 h.

The cooled solution was filtered and the solvent evaporated to leave a residue, which was purified by silica gel chromatography, eluting with dichloromethane/methanol/ammonia in the proportions 98/2/0.2 to 96/4/0.4. 0.96 g (61%) of pure product was obtained in the form of free base. Mp: 205–207° C.

Example 4

Compound N° 48 of Table 1

9-[3-(2-Fluorophenyl)propyl]-7-methoxy-2-(pyridin-4-yl)-6,7,8,9-tetrahydro-4H-pyrimido[1,2-a]pyrimidin-4-one oxalate (1:1)

4.1 9-[3-(2 Fluoraphenyl)propyl]-7-methoxy-2-(pyridin-4-yl)-6,7,8,9-tetrahydro-4H-pyrimido[1,2-a] pyrimidin-4-one oxalate (1:1)

To a suspension containing 0.12 g (0.31 mmol) of 9-[3 (2-fluorophenyl)propyl]-7-hydroxy-2-(pyridin-4-yl)6,7,8,9-tetrahydro-4H-pyrimido[1,2-a]pyrimidinone in 3 ml of dimethylformamide was added 14 mg (0.34 mmol) of a suspension of sodium hydride in mineral oil (60%) and the resulting mixture was stirred at room temperature for 15 min. The mixture was cooled to −20° C. and treated with 19.6 μL (0.31 mmol) of iodomethane. Stirring was continued for 1 h. Water was added and the organic phase was separated. The solvent was evaporated to leave a residue, which was purified by silica gel chromatography, eluting with dichloromethane/methanol/ammonia in the proportions 98/2/0.2. 0.1 g (85%) of pure product was obtained and transformed into a monooxalate salt by treatment with one equivalent of oxalic acid 0.085 g (65%). Mp: 164–166° C.

Example 5

Compound N° 4 of Table 1

9-(2-Oxo-2-phenyl-ethyl)-7,7difluoro-2-(pyridin-4-yl)-6,7,8,9-tetrahydro-4H-pyrimido[1,2-a]pyrimidin-4-one

5.1 5,5-Difluoro-1,4,5,6-tetrahydro-2-pyrimidinamine

The product was obtained by analogy with the method described in 2.1 and using 2,2-difluoro-1,3-propandiamine (Tetrahedron (1994) 50(29), 8617–8632) and was used as such in the next step.

5.2 7,7-Difluoro-2-(pyridin-4-yl)-6,7,8,9-tetrahydro-4H-pyrimido[1,2-a]pyrimidin-4-one The product was obtained by analogy with step N° 1.1 and using the intermediate from step N° 5.2. Mp.: 239–240° C.

5.3 9-(2-Oxo-2-phenyl-ethyl)-7,7-difluoro-2-(pyridin-4-yl)-6,7,8,9-tetrahydro-4H-pyrimido[1,2-a]pyrimidin-4-one By analogy with the method described in step N° 2.3 the compound was obtained as a free base. Mp.: 217–219° C.

Example 6

Compound N° 6 of Table 1

9-(2-Oxo-2-phenyl-ethyl)-3-fluoro-7,7-dimethyl-2-(pyridin-4-yl)-6,7,8,9-tetrahydro-4H-pyrimido[1,2-a] pyrimidin-4-one hydrochloride (1:1)

6.1 Ethyl 2-fluoro-3-oxo-3-pyridin-4-yl propanoate hydrochloride (cf. Tetrahedron Letters, Vol.30, N° 45, pp 6113–6116, 1989)

To a solution of 134.88 ml (0.54 mol) of tri-n-butylphosphine in 500 ml of anhydrous tetrahydrofuran under argon was added 63.8 ml (0.54 mol) of ethyl bromofluoroacetate and the resulting mixture stirred at room temperature during 40 h.

The reaction mixture was cooled to −78° C. and 237.58 ml (0.594 mol) of n-butyl lithium (2.5M in hexane) was added dropwise and allowed to stir for 1 h. 76.44 g (0.54 mol) of isonicotinoyl chloride (Heterocyclic Chemistry, 18, 519, 1981) was added and the mixture allowed to stir for 1 h. The temperature was allowed to increase to room temperature during the night and at 0° C., 700 ml of a 5% aqueous solution of sodium bicarbonate was added and the resulting mixture allowed to stir overnight The tetrahydrofuran was evaporated under reduced pressure and the resulting aqueous phase was extracted with dichloromethane, washed with brine and dried over anhydrous sodium sulfate and evaporated to give a dark brown residue. Flash chromatography on silica gel (eluant cyclohexane/ethyl acetate 90/10 to 50/50). This product was treated with a solution of hydrochloric acid in isopropanol (6N) to give 20 g (17%) of product. Mp. 142–144° C.

6.2 7,7-Dimethyl-3-fluoro-2-(pyridin-4-yl)-6,7,8,9-tetrahydro-4H-pyrimido[1,2-a]pyrimidin-4-one A mixture of 5.0 g (20.19 mmol) of ethyl pyridin-4-yl-3-oxo-2-fluoropropanoate hydrochloride, 3.30 g (20.19 mmol) 5,5-dimethyl-1,4,5,6-tetrahydro-2-pyrimidinamine hydrochloride (prepared by analogy to the method described in U.S. Pat. No. 4,262,122 and 8.37 g (60.57 mmol) of potassium carbonate in 30 ml of ethanol were heated at reflux temperature during 18 h.

The cooled suspension was filtered and the solvent removed by evaporation. The residue obtained was treated with dichloromethane and washed with water. The organic phase was dried and evaporated to give 1.9 g (34%) of product as a beige solid. Mp.: 190–192° C.

6.3 9-(2-Oxo-2-phenyl-ethyl)-3-fluoro-7,7-dimethyl-2-(pyridin-4-yl)-6,7,8,9-tetrahydro-4H-pyrimido[1,2-a]pyrimidin-4-one hydrochloride (1:1)

A suspension of 0.30 g (1.09 mmol) of 7,7-dimethyl-3-fluoro-2-(pyridin-4-yl)-6,7,8,9-tetrahydro-4H-pyrimido[1,2-a]pyrimidin-4-one in 6 ml of anhydrous dimethylformamide was treated with 53 mg (1.31 mmol) of sodium hydride (60% suspension in mineral oil) and the resulting mixture was stirred for 10 min. 0.261 g (1.31 mmol) of phenacyl bromide was added and the reaction mixture stirred at room temperature for 3 h.

The solution was treated with water and extracted with ethyl acetate. The organic phase was dried and evaporated to give crude product, which was purified by silica gel chromatography, eluting with dichloromethane/methanol in the proportions 98/2 to 90/10 to give 0.10 g of pure product obtained in the form of free base which was transformed into the hydrochloride salt. Mp: 236–238° C.

Example 7

Compound N° 21 in Table 1 9-(2-Oxo-2-phenyl-ethyl)-7,7-dimethyl-3-bromo-2-(pyridin-4-yl)-6,7,8,9-tetrahydro-4H-pyrimido[1,2-a]pyrimidin-4-one

7.1 3-Bromo-7,7-dimethyl-2-(pyridin-4-yl)-6,7,8,9-tetrahydro-4H-pyrimido[1,2-a]pyrimidin-4-one hydrobromide (1:1)

To a solution of 3.0 g (11.7 mmol) of 7,7-dimethyl-2-(pyridin-4-yl)-6,7,8,9-tetrahydro-4H-pyrimido[1,2-a]pyrimidin-4-one in 75 ml of acetic acid was added dropwise 0.6 ml (11.7 mmol) of bromine. The mixture was allowed to stir at room temperature for 2 h.

The precipitated solid was recovered by filtration, washed with ether and dried affording 4.53 g (97%) of product as a yellow solid. Mp.: 270–272° C.

9-(2-Oxo-2-phenyl-ethyl)-7,7-dimethyl-3-bromo-2-(pyridin-4-yl)-6,7,8,9-tetrahydro-4H-pyrimido[1,2-a]pyrimidin-4-one A solution containing 4.15 g (10.43 mmol) of 3-bromo-7,7-dimethyl-2-(pyridin-4-yl)-6,7,8,9-tetrahydro-4H-pyrimido[1,2-a]pyrimidin-4-one hydrobromide in water was treated with an excess of an aqueous solution of sodium hydroxide. The free base was extracted with dichloromethane and the organics dried and evaporated. The residue was solubilized in 25 ml of anhydrous dimethylformamide and 0.542 g (13.56 mmol) of sodium hydride (60% suspension in mineral oil) and the resulting mixture was stirred for 40 min. 2.43 g (12.49 mmol) of phenacyl bromide was added and the reaction mixture stirred at room temperature for 5 h.

The solution was treated with water at 0° C. and the precipitate which formed was recovered by filtration and dried, 3.5 g (74%). Mp: 223–225° C.

Example 8

Compound N° 38 in Table 1 9-(2-Oxo-2-phenyl-ethyl)-3-methyl-2-(pyridin-4-yl)-6,7,8,9-tetrahydro-4H-pyrimido[1,2-a]pyrimidin-4-one

8.1 3-Methyl-2-(pyridin-4-yl)-6,7,8,9-tetrahydro-4H-pyrimido[1,2-a]pyrimidin-4-one A mixture of 14.0 g (67.56 mmol) of ethyl 2-methyl-3-(pyridin-4-yl)-3-oxopropionate (prepared by analogy to the method described in French Patent FR 2529786), 9.16 g (67.66 mmol) of 1,4,5,6-tetrahydro-2-pyrimidinamine monohydrochloride (prepared according to J. Org. Chem. 1955, 20, 829) and 9.33 g (67.66 mmol) of potassium carbonate in 300 ml of ethanol was heated at reflux temperature during 12 h.

The cooled suspension was filtered and the solvent removed by evaporation. The residue obtained was treated with water and the precipitate filtered and dried. The product was thus obtained as a brown solid. 10.5 g (64%) Mp.: 242–243° C.

8.2 9-(2-Oxo-2-phenyl-ethyl)-3-methyl-2-(pyridin-4-yl)-6,7,8,9-tetrahydro-4H-pyrimido[1,2-a]pyrimidin-4-one A suspension of 0.25 g (1.03 mmol) of 3-methyl-2-(pyridin-4-yl)-6,7,8,9-tetrahydro-4H-pyrimido[1,2-a]pyrimidin-4-one in 4 ml of anhydrous dimethylformamide was treated with 45 mg (1.03 mmol) of sodium hydride (50% suspension in mineral oil) and the resulting mixture was stirred for 1 h. 0.205 g (1.03 mmol) of phenacyl bromide was added and the reaction mixture stirred at room temperature for 5 h.

The solution was treated with water and extracted with ethyl acetate. The organic phase was dried and evaporated to give crude product, which was purified by silica gel chromatography, eluting with dichloromethane/methanol/ammonia in the proportions 98/2/0.2 to give 0.10 g (27%) of pure product obtained in the form of free base. Mp: 190–192° C.

Example 9

Compound N° 2 in Table 1 9-(2-Oxo-2-phenyl-ethyl)-7,7-dimethyl-2-(pyridin-4-yl)-6,7,8,9-tetrahydro-4H-pyrimido[1,2-a]pyrimidin-4-one hydrochloride(1:1)

The product was obtained by using the method described in step 2.3 and employing 7,7-dimethyl-2-(pyridin-4-yl)-6,7,8,9-tetrahydro-4H-pyrimido [1,2-a]pyrimidin-4-one. Mp.: 283–285° C.

Example 10

Compound N° 3 in Table 1 9-(2-Hydroxy-2-phenyl-ethyl)-7,7 dimethyl-2(pyridin-4-yl)-6,7,8,9-tetrahydro-4H-pyrimido[1,2-a]pyrimidin-4-one To a solution of 2.0 g (5.34 mmol) of 9-(2-Oxo-2-phenyl-ethyl)-7,7-dimethyl-2-((pyridin-4-yl))-6,7,8,9-tetrahydro-4H-pyrimido[1,2-a]pyrimidin-4-one obtained in step 9 in 100 ml of methanol at 0° C. was added 0.24 g (6.41 mmol) of sodium borohydride. Stirring was maintained for 30 min. and the solvent was removed by evaporation.

Water was added and the resulting mixture extracted with dichloromethane. The organics were dried and evaporated and the residue was triturated with ethyl acetate to give 1.66 g (83%) of product. The Z-but-2-endioate salt of the product was characterized. Mp.: 195–197° C.

Example 11

Compound N° 34 in Table 1 9-(2-Amino-2-phenyl-ethyl)-7,7-dimethyl-2-(pyridin-4-yl)-6,7,8,9-tetrahydro-4H-pyrimido[1,2-a]pyrimidin-4-one hydrochloride (1:1)

11.1 2-[2-(3,3-Dimethyl-6-oxo-8-(pyridin-4-yl)-3,4-dihydro-2H,6H-pyrimido[1,2-a]pyrimidin-1-yl)-1-phenyl-ethyl]-isoindole-1,3-dione To a solution of 0.2 g (0.531 mmol) of 9-(2-Hydroxy-2-phenyl-ethyl)-7,7-dimethyl-2-(pyridin-4-yl)-6,7,8,9-tetrahydro-4H-pyrimido[1,2-a]pyrimidin-4-one, 0.080 g (0.584 mmol) of phthalimide and 0.195 g (0.742 mmol) in 30 ml of anhydrous tetrahydrofuran at 0° C. was added 0.142 ml (0.903 mmol) of diethyl azodicarboxylate and the reaction mixture stirred for 18 h.

The solvent was evaporated and the residue was purified by chromatography on silica gel eluting with dichloromethane/methanol/diethylamine in the proportions 98/2/0.2 to give 0.06 g (22%) of product.

11.2 9-(2-Amino-2-phenyl-ethyl)-7,7-dimethyl-2-(pyridin-4-yl)-6,7,8,9-tetrahydro-4H-pyrimido[1,2-a]pyrimidin-4-one hydrochloride (1:1)

A solution of 0.470 g (0.929 mmol) of 2-[2-(3,3-dimethyl-6-oxo-8-(pyridin-4-yl)-3,4-dihydro-2H,6H-pyrimido[1,2-a]pyrimidin-1-yl)-1-phenyl-ethyl]-isoindole-1,3-dione in 50 ml of ethanol containing 0.452 ml (9.29 mmol) of hydrazine hydrate was heated at reflux temperature for 18 hr.

The cooled solution was filtered and the solvent removed by evaporation. The residue was purified by chromatography on silica gel eluting with ethyl acetate/methanol/diethylamine in the proportions 95/5/0.5 to 94/6/0.6. The free base recovered was transformed into the hydrochloride salt to give 0.283 g (68%) of product. Mp.: 227–231° C.

Example 12

Compound N° 1 in Table 2 [3-(2-Fluoro-phenyl)-propyl]-2,2-dimethyl-7-(pyridin-4-yl)-2,3-dihydro-1H-imidazo[1,2-a]pyrimidin-5-one hydrochloride (1:2)

12.1 5,5-Dimethyl-4,5-dihydro-1H-imidazol-2-ylamine hydrobromide (1:1)

To a solution of 15 g (0.17 mol) of 1,2-diamino-2-methylpropane in 150 ml of water at 0° C., was added 18 g (0.17 mol) of cyanogen bromide portionwise and the temperature was allowed to warm to room temperature during 4 h. The water was removed by evaporation and ethanol was added and evaporated. Trituration in a mixture of diethyl ether and ethanol gave 29.5 g (89%) of product as an amorphous hygroscopic solid.

12.2 2,2-Dimethyl-7-(pyridin-4-yl)-2,3-dihydro-1H-imidazo[1,2-a]pyrimidin-5-one A suspension of 4.5 g (23.2 mmol) of 5,5-dimethyl-4,5-dihydro-1H-imidazol-2-ylamine hydrobromide, 2.99 g (15.46 mmol) of ethyl 3-(pyridin-4-yl)-3-oxopropionate and 4.27 g (30.89 mmol) of potassium carbonate in 100 ml of ethanol was heated at reflux temperature for 18 h.

The cooled suspension was filtered and the solvents evaporated. The residue obtained was dissolved in dichloromethane and washed with water. The solvent was evaporated to give 2.5 g (67%) of pure product. Mp.: 226–228° C.

12.3 [3-(2-Fluoro-phenyl)-propyl]-2,2-dimethyl-7-(pyridin-4-yl)-2,3-dihydro-1H-imidazo[1,2-a]pyrimidin-5-one hydrochloride (1:2)

A suspension of 0.3 g (1.23 mmol) of 2,2-dimethyl-7-(pyridin-4-yl)-2,3-dihydro-1H-imidazo[1,2-a]pyrimidin-5-one in 6 ml of anhydrous dimethylformamide was treated with 64 mg (1.6 mmol) of sodium hydride (60% suspension in mineral oil) The mixture was heated at 60° C. for 10 min. and then 0.322 g (1.48 mmol) of 3-(2-fluorophenyl)propyl bromide was added and the mixture heated at 120° C. during 1 h.

The cooled solution was treated with water and extracted with ethyl acetate. The solvent was evaporated to leave a residue which was purified by silica gel chromatography, eluting with dichloromethane/methanol in the proportions 98/2 to 95/5 to obtain 0.248 g (55%) of pure product was obtained in the form of free base which was transformed into the dihydrochloride salt Mp: 140–142° C.

Example 13

Compound No. 1 of Table 3 9-[2-(4-Fluoro-2-methoxy-phenyl)-ethyl]-8-methyl-2-(pyridin-4-yl)-6,7,8,9-tetrahydro-pyrimido[1,2-a]pyrimidin-4-one

13.1 8-Methyl-2-(pyridin-4-yl)-6,7,8,9-tetrahydro-pyrimido[1,2-a]pyrimidin-4-one A mixture of 6 g (31.0 mmol) of ethyl 3-(pyridin-4-yl)-3-oxopropionate, 4.6 g (31.0 mmol) 6-methyl-1,4,5,6-tetrahydro-pyrimidin-2-ylamine hydrochloride (prepared according to *J. Org. Chem.*, 20, 1955, 829–838) and 6.44 g (46.0 mmol) of potassium carbonate in 50 ml of ethanol were heated at reflux temperature during 18 h.

The reaction mixture was cooled and the solvent removed by evaporation. The residue obtained was treated with water and the precipitate recovered by filtration to give 3.85 g (51%) of product. Mp.: 245–247° C.

13.2 (4-Fluoro-2-methoxy-phenyl)-acetic acid methyl ester

To a suspension of 14.34 g (32.47 mmol) of lead (IV) acetate in 100 ml of anhydrous toluene was added a mixture of 5.2 g (30.92 mmol) of 1-(4fluoro-2-methoxy-phenyl)-ethanone and 15.02 ml (123.13 mmol) of boron trifluoride etherate in 9 ml of methanol. The reaction mixture is further stirred at room temperature for 16 h. Water was added to the cooled mixture and the resulting solution extracted with toluene. The extracts were washed with saturated sodium hydrogen carbonate solution, saturated sodium chloride solution and dried with sodium sulphate. The solvent was evaporated to dryness to give 6 g of product as an oil, which was used in the subsequent step without further purification.

13.3 2-(4-Fluoro-2-methoxy-phenyl)-ethanol

To a suspension of 1.72 g (45.41 mmol) of lithium aluminum hydride in 120 ml of tetrahydrofuran at 0° C. was added dropwise 6 g (30.27 mmol) of dissolved in 120 ml of (4-Fluoro-2-methoxy-phenyl)-acetic acid methyl ester and the resulting mixture stirred at room temperature for 1 h.

The reaction mixture was diluted with 100 ml of diethylether at 0° C. and treated with excess of a saturated aqueous solution of sodium sulfate. Further solid sodium sulfate was added and the organic phase was filtered to remove salts. The solvent was evaporated to dryness to give 5.1 g (99%) of product as an oil.

13.4 Methanesulfonic acid 2-(4-fluoro-2-methoxy-phenyl)-ethyl ester

To a solution of 5.1 g (29.97 mmol) of 2-(4-Fluoro-2-methoxy-phenyl)-ethanol in 30 ml of anhydrous dichloromethane was added at 0° C. 6.26 ml (44.95 mmol) of triethylamine and 3.5 ml (44.95 mmol) of methanesulfonyl chloride. The resulting mixture was stirred at 0° C. for 1 h. The mixture was then diluted with water and dichloromethane and extracted with dichloromethane. Organic layer was dried and evaporated to give 7 g(100%) of methanesulfonic acid 2-(4-fluoro-2-methoxy-phenyl)-ethyl ester.

13.5 9-[2-(4-Fluoro-2-methoxy-phenyl)-ethyl]-8-methyl-2-(pyridin-4-yl)-6,7,8,9-tetrahydro-pyrimido[1,2-a]pyrimidin-4-one hydrochloride (1:1)

To a solution of 0.25 g (1.03 mmol) of 8-methyl-2-(pyridin-4-yl)-6,7,8,9-tetrahydro-pyrimido[1,2-a]pyrimidin-4-one in 4 ml of anhydrous dimethylformamide was added 0.046 mg (1.14 mmol) of sodium hydride (60% suspension in mineral oil) and the mixture allowed to stir at 50° C. for 20 min. 0.282 g (1.14 mmol) of methanesulfonic acid 2-(4-fluoro-2-methoxy-phenyl)-ethyl ester was added and stirring continued for 18 h.

Water was added and the mixture extracted with dichloromethane. The extracts were washed with a saturated aqueous solution of sodium chloride, dried and evaporated to give crude product. Purification by chromatography on silica gel eluting with a mixture of dichloromethane/methanol in the proportions 100/0 to 96/4. The compound was obtained in the form of free base which was transformed into its hydrochloride salt to give 0.192 g (43%) of pure product. Mp.: 206–208° C.

Example 14

Compound No. 2 in Table 3 9-[2-(4-Fluoro-2-methoxy-phenyl)-ethyl]-8,8-dimethyl-2-(pyridin-4-yl)-6,7,8,9-tetrahydro-pyrimido[1,2-a]pyrimidin-4-one

14.1 8,8-Dimethyl-2-(pyridinyl)-6,7,8,9-tetrahydro-pyrimido[1,2-a]pyrimidin-4-one A mixture of 7.68 g (39.8 mmol) of ethyl 3-(pyridin-4-yl)-3-oxopropionate, 7.9 g (37.9 mmol) 6,6-dimethyl-1,4,5,6-tetrahydro-pyrimidin-2-ylamine hydrobromide (prepared according to *Bull. Soc. Chim. Belg.*, 1950, 59, 573–587) and 11 g (79.5 mmol) of potassium carbonate in 80 ml of ethanol were heated at reflux temperature during 18 h.

The reaction mixture was cooled and the solvent removed by evaporation. The residue obtained was treated with water and the precipitate recovered by filtration to give 3.21 g (33%) of product. Mp.: 345–347° C.

14.2 9-[2-(4-Fluoro-2-methoxy-phenyl)-ethyl]-8,8-dimethyl-2-(pyridin-4-yl)-6,7,8,9-tetrahydro-pyrimido[1,2-a]pyrimidin-4-one To a solution of 0.222 g (0.87 mmol) of 8,8-dimethyl-2-(pyridin-4-yl)-6,7,8,9-tetrahydro-pyrimido[1,2-a]pyrimidin-4-one in 5 ml of anhydrous dimethylformamide was added 0.039 g (0.95 mmol) of sodium hydride (60% suspension in mineral oil) and the mixture allowed to stir at 50° C. for 20 min. 0.236 g (0.95 mmol) of methanesulfonic acid 2-(4-fluoro-2-methoxy-phenyl)-ethyl ester was added and stirring continued for 18 h.

Water was added and the mixture extracted with dichloromethane. The extracts were washed with a saturated aqueous solution of sodium chloride, dried and evaporated to give crude product. Purification by chromatography on silica gel eluting with a mixture of dichloromethane/methanol in the proportions 100/0 to 96/4 gave 0.18 g (50%) of pure product. Mp.: 217–219° C.

Example 15

Compound No. 8 in Table 3 9-(2(S)-Hydroxy-2-phenyl-ethyl)-8,8-dimethyl-2-pyridin-4-yl-6,7,8,9-tetrahydro-pyrimido[1,2-a]pyrimidin-4-one hydrochloride (1:1)

To a solution of 1 g (3.90 mmol) of 8,8-dimethyl-2-pyridin-4-yl-6,7,8,9-tetrahydro-pyrimido[1,2-a]pyrimidin-4-one in 12 ml of anhydrous dimethylformamide was added 0.343 g (8.58 mmol) of sodium hydride (60% suspension in mineral oil) and the mixture allowed to stir at 50° C. for 1 h. 0.794 g (5.07 mmol) of (1-S)-2-chloro-1-phenyl ethanol was added and the mixture allowed to stir at 120° C. for 12 h.

Water was added and the mixture extracted with ethyl acetate. The extracts were washed with a saturated aqueous solution of sodium chloride, dried and evaporated to give crude product. Purification by chromatography on silica gel eluting with a mixture of ethyl acetate/ethanol in the proportions 100/0 to 96/4. The compound was obtained in the form of free base which was transformed into its hydrochloride salt to give 0.87 g (59%) of pure product. Mp: 204–206° C., $[\alpha]_D$=–20.70 (c=0.855, $CH_3OH$).

Example 16

Compound No. 10 in Table 3 8,8-Dimethyl-9-(2-oxo-2-phenyl-ethyl)-2-pyridin-4-yl-6,7,8,9-tetrahydro-pyrimido[1,2-a]pyrimidin-4-one hydrochloride (1:1).

To a solution of 0.12 ml (1.65 mmol) of dimethyl sulphoxide in 3 ml of anhydrous dichloromethane at −78° C. was added 0.21 ml (1.46 mmol) of trifluoroacetic anhydride in 1 ml of anhydrous dichloromethane and the mixture allowed to stir at −78° C. for 20 min. 0.1 g (0.27 mmol) of 9-(2(S)-hydroxy-2-phenyl-ethyl)-8,8-dimethyl-2-pyridin-4-yl-6,7,8,9-tetrahydro-pyrimido[1,2-a]pyrimidin-4-one in 2 ml of anhydrous dichloromethane was added at −78° C. and stirring continued for 30 min.

0.31 ml (2.23 mmol) of triethylamine was added and the mixture allowed to stir at room temperature for 12 h. Water was added and the mixture extracted with ethyl acetate, the extracts were washed with a saturated aqueous solution of ammonium chloride, a saturated aqueous solution of sodium chloride, dried and evaporated to give crude product. Purification by chromatography on silica gel eluting with a mixture of dichloromethane/methanol/ammonium hydroxide in the proportions 95/5/0.5. The compound was obtained in the form of free base which was transformed into its hydrochloride salt to give 0.026 g (24%) of pure product. Mp: 247–249° C.

Example 17

Compound No. 16 in Table 3

8-Ethyl-9-(2-oxo-2-phenyl-ethyl)-2-pyridin-4-yl-6,7,8,9-tetrahydro-pyrimido[1,2-a]pyrimidin-4-one hydrochloride (1:1).

17.1 8-Ethyl-2-pyridin-4-yl-6,7,8,9-tetrahydro-pyrimido[1,2-a]pyrimidin-4-one

A mixture of 5 g (25.88 mmol) of ethyl 3-(4-pyridinyl)-3-oxopropionate, 3.85 g (23.53 mmol) of 6-ethyl-1,4,5,6-tetrahydro-pyrimidin-2-ylamine hydrochloride (prepared according to *J. Org. Chem.*, 20, 1955, 829–838) and 6.83 g (49.41 mmol) of potassium carbonate in 51 ml of ethanol were heated at reflux temperature during 18 h.

The reaction mixture was cooled and the solvent removed by evaporation. The residue obtained was treated with water and the precipitate recovered by filtration to give 4.1 g (68%) of product. Mp.: 244–246° C.

17.2 8-Ethyl-9-(2-oxo-2-phenyl-ethyl)-2-pyridin-4-yl-6,7,8,9-tetrahydro-pyrimido[1,2-a]pyrimidin-4-one hydrochloride (1:1).

To a solution of 0.3 g (1.17 mmol) of 8-ethyl-2-pyridin-4-yl-6,7,8,9-tetrahydro-pyrimido[1,2-a]pyrimidin-4-one in 6 ml of anhydrous dimethylformamide was added 0.343 g (8.58 mmol) of sodium hydride (60% suspension in mineral oil) and the mixture allowed to stir at 50° C. for 15 min. At 0° C., 0.303 g (1.52 mmol) of phenacyl bromide was added the mixture allowed to stir at 0 C. for 3 h and the temperature was allowed to warm to room temperature during 12 h.

Water was added and the mixture extracted with ethyl acetate. The extracts were washed with a saturated aqueous solution of sodium chloride, dried and evaporated to give crude product. Purification by chromatography on silica gel eluting with a mixture of dichloromethane/methanol in the proportions 100/0 to 96/4. The compound was obtained in the form of free base which was transformed into its hydrochloride salt to give 0.134 g (28%) of pure product. Mp: 189–191° C.

Example 18

Compound No. 18 in Table 3 3-Fluoro-8-methyl-9-(2-oxo-2-phenyl-ethyl)-2-(pyridin-4-yl)-6,7,8,9-tetrahydro-pyrimido[1,2-a]pyrimidin-4-one.

18.1 3-Fluoro-8-methyl-2-pyridin-4-yl-6,7,8,9-tetrahydro-pyrimido[1,2-a]pyrimidin-4-one.

The product was obtained by analogy with step N° 13.1 and using the intermediate from step N° 6.1. Mp.: 274–276° C.

18.2 3-Fluoro-8-methyl-9-(2-oxo-2-phenyl-ethyl)-2-(pyridin-4-yl)-6,7,8,9-tetrahydro-pyrimido[1,2-a] pyrimidin-4-one.

The product was obtained by analogy with step N° 17.2. Mp.: 201–202° C.

A list of chemical structures and physical data for compounds of the aforementioned formula (I) illustrating the present invention is given in tables 1 and 2. The compounds have been prepared according to the methods of the example.

In the tables, R1 is an unsubstituted 4-pyridine ring (4-py), Ph represents a phenyl group, Et represents an ethyl group, Me represents a methyl group; in the column "X", when X represents two hydrogen atoms, only "H" is indicated, (S), (R) or (Rac.) indicates in the column "Y" the stereochemistry respectively, (S), (R) or (Rac.) of the carbon atom.

(rac.) means racemic mixture (R) means absolute R configuration (S) means absolute S configuration In table 1, for compounds of formula (I) "m" and "p" equal 1; in table 2, for compounds of formula (I), "m" equals 0 and "p") equals 1 and in table 3 for compounds of formula (I) "m" equals 0 and "p" equals 2.

TABLE 1

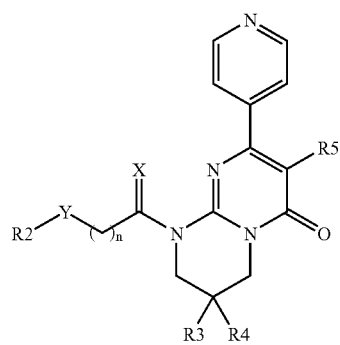

| N° | X | Y | R2 | R3 | R4 | R5 | n | Mp ° C. | salt |
|---|---|---|---|---|---|---|---|---|---|
| 1 | H | CH₂ | 2-F-phenyl | CH₃ | CH₃ | H | 1 | 250–252 | (1:1)hydrochloride |
| 2 | H | CO | Ph | CH₃ | CH₃ | H | 0 | 283–255 | (1:1)hydrochloride |
| 3 | H | CH(OH) (rac.) | Ph | CH₃ | CH₃ | H | 0 | 195–197 | (1:1)(Z)-but-2-enedioate |
| 4 | H | CO | Ph | F | F | H | 0 | 217–219 | Free base |
| 5 | H | CH(OH) (S) | Ph | F | F | H | 0 | 179–180 | Free base |
| 6 | H | CO | Ph | CH₃ | CH₃ | F | 0 | 236–238 | (1:1)hydrochloride |
| 7 | H | CO | 3-Cl-phenyl | CH₃ | CH₃ | H | 0 | 238–240 | (1:1)hydrochloride |
| 8 | H | CH(OH) (S) | Ph | CH₃ | CH₃ | H | 0 | 234–236 | (1:1)hydrochloride |
| 9 | H | CO | 3-F-phenyl | CH₃ | CH₃ | H | 0 | 233–235 | (1:1)hydrochloride |
| 10 | H | CH(OH) (rac.) | 3-Cl-phenyl | CH₃ | CH₃ | H | 0 | 195–197 | Free base |
| 11 | H | CH(OH) (rac.) | 3-F-phenyl | CH₃ | CH₃ | H | 0 | 198–199 | Free base |
| 12 | H | CH(OH) (S) | Ph | CH₃ | CH₃ | F | 0 | 228–230 | (1:1)hydrochloride |

TABLE 1-continued
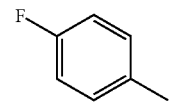
(I)
| N° | X | Y | R2 | R3 | R4 | R5 | n | Mp °C. | salt |
|---|---|---|---|---|---|---|---|---|---|
| 13 | H | CO | 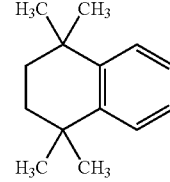 | CH₃ | CH₃ | H | 0 | 256–257 | (1:1)hydrochloride |
| 14 | H | CO | 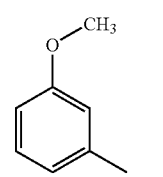 | CH₃ | CH₃ | H | 0 | 237–238 | (1:1)hydrochloride |
| 15 | H | CO | 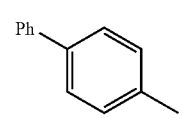 | CH₃ | CH₃ | H | 0 | 203–204 | (1:1)hydrochloride |
| 16 | H | CO | 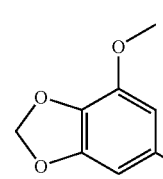 | CH₃ | CH₃ | H | 0 | 232–233 | (1:1)hydrochloride |
| 17 | H,CH₃ (rac.) | CO | 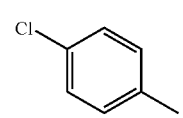 | CH₃ | CH₃ | H | 0 | 241–242 | (1:1)hydrochloride |
| 18 | H | CO | 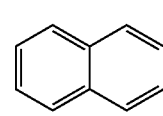 | CH₃ | CH₃ | H | 0 | 257–258 | (1:1)hydrochloride |
| 19 | H | CO | 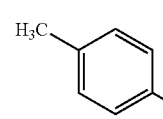 | CH₃ | CH₃ | H | 0 | 232–233 | (1:1)hydrochloride |
| 20 | H | CO |  | CH₃ | CH₃ | H | 0 | 256–257 | (1:1)hydrochloride |

TABLE 1-continued (I)

| N° | X | Y | R2 | R3 | R4 | R5 | n | Mp ° C. | salt |
|---|---|---|---|---|---|---|---|---|---|
| 21 | H | CO | Ph | CH₃ | CH₃ | Br | 0 | 223–225 | Free base |
| 22 | H | CH(OMe) (S) | Ph | CH₃ | CH₃ | H | 0 | 145–146 | Free base |
| 23 | O | CH₂ | Ph | CH₃ | CH₃ | H | 1 | 134–136 | Free base |
| 24 | H | C(OH)(CH₃) (rac.) | Ph | CH₃ | CH₃ | H | 0 | 208–210 | Free base |
| 25 | O | C(OMe)(CF₃) (rac.) | Ph | CH₃ | CH₃ | H | 0 | 162–163 | Free base |
| 26 | H | C(OH)(Ph) (rac.) | Ph | CH₃ | CH₃ | H | 0 | 270–272 | Free base |
| 27 | H | N-OH (oxime group) | Ph | CH₃ | CH₃ | H | 0 | 249–250 | Freebase |
| 28 | H | C(OH)(CH₃) (rac.) | Ph | CH₃ | CH₃ | F | 0 | 230–232 | (1:1)hydrochloride |
| 29 | H | dioxolane | Ph | CH₃ | CH₃ | H | 0 | 214–215 | Free base |
| 30 | H | CH(OH) (rac.) | CH₂OH | CH₃ | CH₃ | H | 0 | 242–243 | (1:1)hydrochloride |
| 31 | H | C(H)(OMe) (R) | Ph | CH₃ | CH₃ | H | 0 | 190–192 | (1:1)hydrochloride |
| 32 | H | C(H)(OH) (rac.) | PhNHCH₂ | CH₃ | CH₃ | H | 0 | 199–200 | Free base |
| 33 | H | C(H)(NHAc) (rac.) | Ph | CH₃ | CH₃ | H | 0 | 246–247 | Free base |
| 34 | H | C(H)(NH₂) (rac.) | Ph | CH₃ | CH₃ | H | 0 | 227–231 | (1:1)hydrochloride |
| 35 | H | C(H)(OH) (rac.) | PhOCH(CH₃) | CH₃ | CH₃ | H | 0 | 156–157 | Free base |
| 36 | H | CO | Ph | H | H | F | 0 | 264–266 | (1:1)hydrochloride |
| 37 | H | CO | 3-F-C₆H₄ | H | H | F | 0 | 260–262 | (1:1)hydrochloride |

TABLE 1-continued (I)

| N° | X | Y | R2 | R3 | R4 | R5 | n | Mp ° C. | salt |
|---|---|---|---|---|---|---|---|---|---|
| 38 | H | CO | Ph | H | H | CH₃ | 0 | 190–192 | Free base |
| 39 | H | CO | Ph | H | H | Cl | 0 | 260–262 | (1:1)hydrochloride |
| 40 | H | CO | Ph | H | H | Br | 0 | 260–262 | (1:1)hydrochloride |
| 41 | H | CO | Ph-NH- (phenyl-NH) | H | H | CH₃ | 0 | 242–243 | Free base |
| 42 | H | C(H)(OH) (S) | Ph | H | H | Cl | 0 | 221–213 | (1:1)hydrochloride |
| 43 | H | C(H)(OH) (S) | Ph | H | H | CH₃ | 0 | 211–213 | (1:1)hydrochloride |
| 44 | H | C(H)(OH) (S) | Ph | H | H | F | 0 | 170–172 | (1:1)hydrochloride |
| 45 | H | C(H)(OMe) (S) | Ph | H | H | F | 0 | 108–110 | (1:1)hydrochloride |
| 46 | H | C(H)(OMe) (R) | Ph | H | H | F | 0 | 202–204 | (1:1)hydrochloride |
| 47 | H | CH₂ | 2-F-phenyl | H | OH (rac) | H | 1 | 205–207 | Free base |
| 48 | H | CH₂ | 2-F-phenyl | H | OMe (rac) | H | 1 | 164–166 | (1:1)oxalate |
| 49 | H | CO | Ph | H | CH₃ (rac) | H | 0 | 202–203 | Free base |
| 50 | H | C(H)(OH) (rac.) | Ph | H | CH₃ (rac) | H | 0 | 174–175 | Free base |
| 51 | H | C(OH)(CH₃) chiral | Ph | CH₃ | CH₃ | H | 0 | 150–151 | Free base |
| 52 | H | C(OH)(CH₃) chiral | Ph | CH₃ | CH₃ | H | 0 | 144–146 | Free base |
| 53 | H | C(H)(OMe) (R) | Ph | CH₃ | CH₃ | H | 0 | 143–145 | Free base |
| 54 | H | CH₂ | 5-F-2-OMe-phenyl | H | H | F | 0 | 190–192 | Free base |
| 55 | H | bond | 2-methylindanyl | CH₃ | CH₃ | H | 0 | 238–240 | (1:1) hydrochloride |

TABLE 1-continued
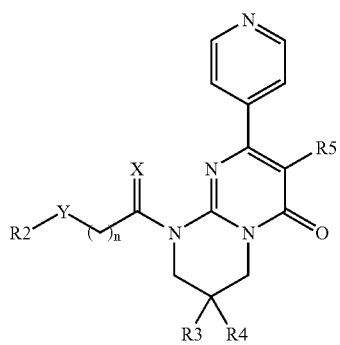
(I)
| N° | X | Y | R2 | R3 | R4 | R5 | n | Mp ° C. | salt |
|---|---|---|---|---|---|---|---|---|---|
| 56 | H | CH₂ | (5-F, 2-Me, OMe-phenyl) | CH₃ | CH₃ | F | 0 | 140–142 | Free base |
| 57 | H | CH₂ | (5-F, 2-Me, OMe-phenyl) | CH₃ | CH₃ | H | 0 | 235–237 | (1:1) hydrochloride |
TABLE 2
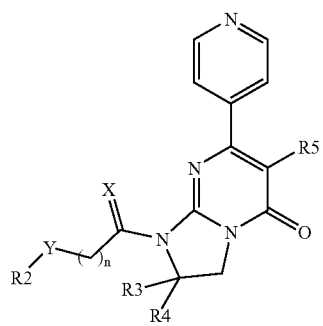
| N° | X | Y | R2 | R3 | R4 | R5 | n | Mp ° C. | Salt |
|---|---|---|---|---|---|---|---|---|---|
| 1 | H | CH₂ | 2-F, 6-Me-phenyl | CH₃ | CH₃ | H | 1 | 140–142 | (1:1)hydrochloride |
| 2 | H | CO | Ph | CH₃ | CH₃ | H | 0 | 314–416 | (1:1)hydrochloride |
| 3 | H | C(H)(OH) (rac.) | Ph | CH₃ | CH₃ | H | 0 | 173–175 | base |
| 4 | H | CO | 4-Cl-phenyl | CH₃ | CH₃ | H | 0 | 268–269 | (1:1)hydrochloride |
| 5 | H | CO | 4-Me-phenyl | CH₃ | CH₃ | H | 0 | 252–253 | (1:1)hydrochloride |

TABLE 2-continued
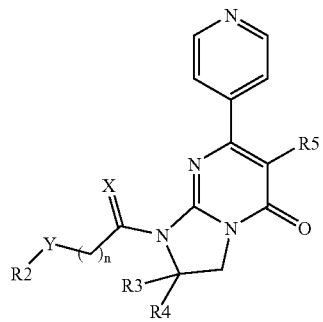
| N° | X | Y | R2 | R3 | R4 | R5 | n | Mp ° C. | Salt |
|---|---|---|---|---|---|---|---|---|---|
| 6 | H | CO | Ph-C6H4- | CH3 | CH3 | H | 0 | 230–231 | (1:1)hydrochloride |
| 7 | H,CH3 (rac.) | CO | (methylenedioxy-methoxyphenyl) | CH3 | CH3 | H | 0 | 259–260 | (1:1)hydrochloride |
| 8 | H | CO | 2-naphthyl | CH3 | CH3 | H | 0 | 186–187 | (1:1)hydrochloride |
| 9 | H | CO | 4-F-C6H4- | CH3 | CH3 | H | 0 | 249 | (1:1)hydrochloride |
| 10 | H | CO | 3-MeO-C6H4- | CH3 | CH3 | H | 0 | 233 | (1:1)hydrochloride |
| 11 | H | CO | 1,1,4,4-tetramethyltetralin-6-yl | CH3 | CH3 | H | 0 | 250–251 | (1:1)hydrochloride |

TABLE 3

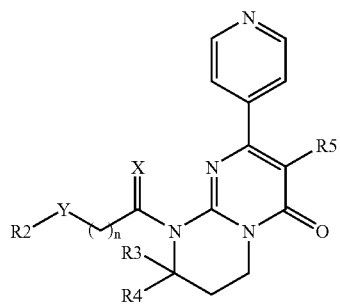
(I)

| N° | X | Y | R2 | R3 | R4 | R5 | n | Mp ° C. | salt |
|---|---|---|---|---|---|---|---|---|---|
| 1 | H | CH₂ | 5-F, 2-OMe, 4-Me-phenyl | CH₃ (Rac.) | H | H | 0 | 206–208 | Hydrochloride (1:1) |
| 2 | H | CH₂ | 5-F, 2-OMe, 4-Me-phenyl | CH₃ | CH₃ | H | 0 | 217–219 | Free base |
| 3 | H | CH₂ | 4-F, 3-Me-phenyl | CH₃ (Rac.) | H | H | 0 | 230–232 | Hydrochloride (1:1) |
| 4 | H | CO | Ph | CH₃ | H | H | 0 | 279–291 | Hydrochloride (1:1) |
| 5 | H | CH₂ | 4-OMe, 3-Me, 5-OMe-phenyl | CH₃ (Rac.) | H | H | 0 | 136–138 | Hydrochloride (1:1) |
| 6 | H | CH₂ | 2-OMe, 3-Me-phenyl | CH₃ (Rac.) | H | H | 0 | 236–238 | Hydrochloride (1:1) |
| 7 | H | C(H)(OH) (S) | Ph | CH₃ (Rac.) | H | H | 0 | 105–107 | Free base |
| 8 | H | C(H)(OH) (S) | Ph | CH₃ | CH₃ | H | 0 | 204–206 | Hydrochloride (1:1) |
| 9 | H | bond | 1-Me-naphthyl | CH₃ (Rac.) | H | H | 0 | 275–277 | Hydrochloride (1:1) |
| 10 | H | CO | Ph | CH₃ | CH₃ | H | 0 | 247–249 | Hydrochloride (1:1) |
| 11 | H | bond | 2-Me-naphthyl | CH₃ (Rac.) | H | H | 0 | 210–212 | Hydrochloride (1:1) |

TABLE 3-continued (I)

| N° | X | Y | R2 | R3 | R4 | R5 | n | Mp ° C. | salt |
|---|---|---|---|---|---|---|---|---|---|
| 12 | H | CO | 3-OMe-phenyl | CH₃ (Rac.) | H | H | 0 | 260–262 | Hydrochloride (1:1) |
| 13 | H | CO | 3-Cl-phenyl | CH₃ (Rac.) | H | H | 0 | 258–260 | Hydrochroride (1:1) |
| 14 | H | C(H)(CH₃) (S) | Ph | CH₃ | CH₃ | H | 0 | 165–167 | Hydrochloride (1:1) |
| 15 | H | C(H)(CH₃) (R) | Ph | CH₃ | CH₃ | H | 0 | 158–160 | Hydrochloride (1:1) |
| 16 | H | CO | Ph | CH₃CH₂ (Rac.) | H | H | 0 | 189–191 | Hydrochloride (1:1) |
| 17 | H | C(H)(OH) (S) | Ph | CH₃CH₂ (Rac.) | H | H | 0 | 176–180 | Hydrochloride (1:1) |
| 18 | H | CO | Ph | CH₃ (Rac.) | H | F | 0 | 201–202 | Free base |
| 19 | H | bond | 1-naphthyl | CH₃ | CH₃ | H | 0 | 178–180 | Hydrochloride (1:1) |
| 20 | H | C(H)(OH) (S) | 4-F-phenyl | CH₃ | CH₃ | H | 0 | 198–200 | Free base |
| 21 | H | C(H)(OH) (Rac.) | 3-F-phenyl | CH₃ (Rac.) | H | H | 0 | 232–234 | Hydrochloride (1:1) |
| 22 | H | C(H)(OH) (Rac.) | 3,5-diCl-phenyl | CH₃ (Rac.) | H | H | 0 | 251–253 | Hydrochloride (1:1) |

TABLE 3-continued
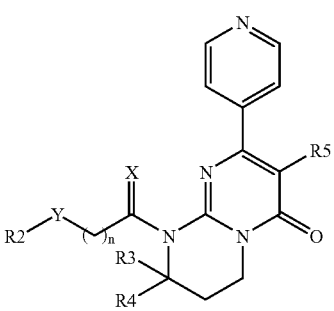
(I)
| N° | X | Y | R2 | R3 | R4 | R5 | n | Mp ° C. | salt |
|---|---|---|---|---|---|---|---|---|---|
| 23 | H | CO | 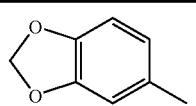 | CH₃ (Rac.) | H | H | 0 | 233–235 | Hydro-chloride (1:1) |
| 24 | H | C(H)(OH) (S) | 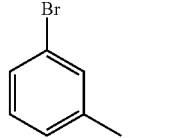 | CH₃ | CH₃ | H | 0 | 244–246 | Hydro-chloride (1:1) |
| 25 | H | CO | 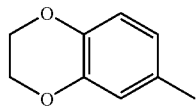 | CH₃ (Rac.) | H | H | 0 | 262–264 | Hydro-chloride (1:1) |
| 26 | H | C(H)(OH) (S) | Ph | CH₃ (Rac.) | H | F | 0 | 170–172 | Free base |
| 27 | H | C(H)(OH) (S) | 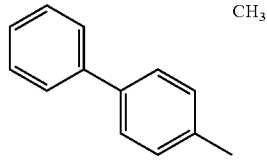 | CH₃ | CH₃ | H | 0 | 188–190 | Hydro-chloride (1:1) |
| 28 | H | C(H)(OH) (S) | 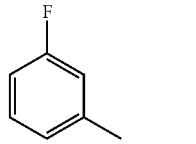 | CH₃ | CH₃ | H | 0 | 217–219 | Hydro-chloride (1:1) |
| 29 | H | C(H)(OH) (S) | 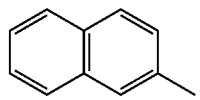 | CH₃ | CH₃ | H | 0 | 231–233 | Hydro-chloride (1:1) |
| 30 | H | C(H)(OH) (S) | 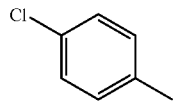 | CH₃ | CH₃ | H | 0 | 209–211 | Hydro-chloride (1:1) |
| 31 | H | C(H)(OH) (S) | 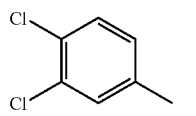 | CH₃ | CH₃ | H | 0 | 257–259 | Hydro-chloride (1:1) |

TABLE 3-continued

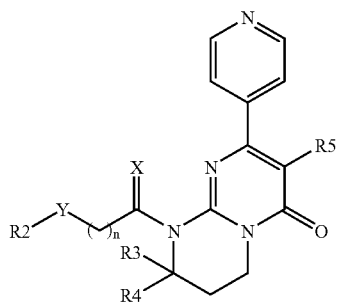

(I)

| N° | X | Y | R2 | R3 | R4 | R5 | n | Mp ° C. | salt |
|----|---|---|-----|-----|-----|----|---|---------|------|
| 32 | H | C(H)(OH) (S) | Me-C₆H₄- (p-tolyl) | CH₃ | CH₃ | H | 0 | 193–195 | Hydrochloride (1:1) |
| 33 | H | CO | Ph | CH₃ (Rac.) | H | Br | 0 | 288–290 | Free base |
| 34 | H | C(H)(OH) (S) | 3-MeO-C₆H₄- | CH₃ | CH₃ | H | 0 | 111–113 | Free base |
| 35 | H | C(H)(OH) (S) | 2,4-diCl-C₆H₃- | CH₃ | CH₃ | H | 0 | 241–243 | Hydrochloride (1:1) |
| 36 | H | C(H)(OH) (S) | Ph | CH₃ | CH₃ | F | 0 | 231–233 | Hydrochloride (1:1) |
| 37 | H | CO | 3-MeO-C₆H₄- | CH₃ | CH₃ | H | 0 | 182–184 | Free base |
| 38 | H | C(H)(OH) (S) | Ph | CH₃ | H | H | 0 | 165–167 (Dia. I) | Free base |
| 39 | H | C(H)(OH) (S) | Ph | H | CH₃ | H | 0 | 118–120 (Dia. II) | Free base |
| 40 | H | CO | Me-C₆H₄- (p-tolyl) | CH3 | CH3 | H | 0 | 204–206 | Free base |
| 41 | H | CO | 3-Br-C₆H₄- | CH₃ | CH₃ | H | 0 | 162–184 | Free base |
| 42 | H | C(H)(OH) (S) | NC-C₆H₄- (4-cyanophenyl) | CH₃ | CH₃ | H | 0 | 241–243 | Hydrochloride (1:1) |

TABLE 3-continued (I)

| N° | X | Y | R2 | R3 | R4 | R5 | n | Mp °C. | salt |
|---|---|---|---|---|---|---|---|---|---|
| 43 | H | CO | 3-fluorophenyl | CH₃ | CH₃ | H | 0 | 196–198 | Hydrochloride (1:1) |
| 44 | H | C(H)(OH) (S) | 3,4-dichlorophenyl | CH₃ | CH₃ | H | 0 | 237–239 | Hydrochloride (1:1) |
| 45 | H | C(H)(OH) (S) | 4-chlorophenyl | Et (Rac) | H | H | 0 | 172–174 | Free base |
| 46 | H | CO | 3-bromophenyl | Et (Rac) | H | H | 0 | 222–224 | Hydrochloride (1:1) |
| 47 | H | CO | 4-chlorophenyl | Et (Rac) | H | H | 0 | 172–174 | Hydrochloride (1:1) |
| 48 | H | C(H)(OH) (S) | 4-methylphenyl | Et (Rac) | H | H | 0 | 208–210 | Hydrochloride (1:1) |

Test Example

Inhibitory Activity of the Medicament of the Present Invention Against GSK3β

Two different protocols can be used.

In a first protocol: 7.5 μM of prephosphorylated GS1 peptide and 10 μM ATP (containing 300,000 cpm of 33P-ATP) were incubated in 25 mM Tris-HCl, pH 7.5, 0.6 mM DTT, 6 mM MgCl₂, 0.6 mM EGTA, 0.05 mg/ml BSA buffer for 1 hour at room temperature in the presence of GSK3β (total reaction volume: 100 microliters).

In a second protocol: 4.1 μM of prephosphorylated GS1 peptide and 42 μM ATP (containing 260,000 cpm 33P-ATP) were incubated in 80 mM Mes-NaOH, pH 6.5, 1 mM Mg acetate, 0.5 mM EGTA, 5 mM 2-mercaptoethanol, 0.02% Tween 20, 10% glycerol buffer for 2 hours at room temperature in the presence of GSK3β.

Inhibitors were solubilized in DMSO (final solvent concentration in the reaction medium, 1%).

The reaction was stopped with 100 microliters of a solution made of 25 g polyphosphoric acid (85% P₂O₅), 126 ml 85% H₃PO₄, H₂O to 500 ml and then diluted to 1:100 before use. An aliquot of the reaction mixture was then transferred to Whatman P81 cation exchange filters and rinsed with the solution described above. Incorporated 33P radioactivity was determined by liquid scintillation spectrometry.

The phosphorylated GS-1 peptide had the following sequence: NH2-YRRMVPPSPSLSRHSSPHQS(P)EDEE-COOH.

The GSK3β inhibitory activity of the compounds of the present invention are expressed in IC$_{50}$, and as an illustration the range of IC$_{50}$'s of the compounds in table 1 is between 4 nanomolar to 2 micromolar concentrations, of the compounds in table 2 is between 30 nanomolar to 2 micromolar concentrations and of the compounds in table three is between 1 nanomolar to 2 micromolar.

Test Example 2

Inhibitory Activity of the Medicament of the Present Invention Against cdk5/p25

The following protocol may be used:

0.4 mg/ml Histone H1 and 10 μM ATP (containing 300,000 cpm of $^{33}$P-ATP) were incubated in 50 mM Hepes, pH 7.2, 1 mM DTT, 1 mM MgCl$_2$, 1 mM EGTA, 0.02% Tween 20 buffer for 1 hour at room temperature in the presence of cdk5/p25 (total reaction volume: 100 microliters).

Inhibitors were solubilized in DMSO (final solvent concentration in the reaction medium, 1%).

The reaction was stopped with 100 microliters of a solution of 25 g polyphosphoric acid (85% P$_2$O$_5$), 126 ml 85% H$_3$PO$_4$, H$_2$O to 500 ml (diluted to 1:100 before use). An aliquot of the reaction mixture was then transferred to Whatman P81 cation exchange filters and rinsed with the solution described above. Incorporated $^{33}$P radioactivity was determined by liquid scintillation spectrometry.

The cdk5/p25 inhibitory activity of the compounds of the present invention are expressed as IC$_{50}$ values. Typically, 3-fold serial dilutions of the inhibitor over at least a 1000-fold concentration range are used.

As an illustration the range of IC$_{50}$'s of the compounds in table 1 is between 200 nanomolar to 5 micromolar concentrations.

As an illustration the specific IC$_{50}$'s of some compounds of the aforementioned formula (I) illustrating the present invention are given in table 4.

TABLE 4

| Table No. | Compound No. | TPK1 IC50 μM | TPK2 IC50 μM |
|---|---|---|---|
| 1 | 37 | 0.004 | 4.6 |
| 3 | 32 | 0.001 | >1.0 |
| 1 | 45 | 0.006 | >1.0 |
| 3 | 7 | 0.004 | 0.344 |
| 1 | 12 | 0.011 | 0.334 |
| 1 | 39 | 0.004 | 0.062 |
| 1 | 5 | 0.060 | 0.067 |
| 1 | 40 | 0.005 | 0.077 |
| 1 | 42 | 0.028 | 0.154 |
| 1 | 44 | 0.006 | >1.0 |

Formulation Example (1) Tablets

The ingredients below were mixed by an ordinary method and compressed by using a conventional apparatus.

| | |
|---|---|
| Compound of Example 1 | 30 mg |
| Crystalline cellulose | 60 mg |
| Corn starch | 100 mg |
| Lactose | 200 mg |
| Magnesium stearate | 4 mg |

(2) Soft Capsules

The ingredients below were mixed by an ordinary method and filled in soft capsules.

| | |
|---|---|
| Compound of Example 1 | 30 mg |
| Olive oil | 300 mg |
| Lecithin | 20 mg |

(1) Parenteral Preparations

The ingredients below were mixed by an ordinary method to prepare injections contained in a 1 ml ampoule.

| | |
|---|---|
| Compound of Example 1 | 3 mg |
| Sodium chloride | 4 mg |
| Distilled water for injection | 1 ml |

INDUSTRIAL APPLICABILITY

The compounds of the present invention have GSK3β or GSK3β and cdk5/p25 inhibitory activity and are useful as an active ingredient of a medicament for preventive and/or therapeutic treatment of diseases caused by abnormal activity of GSK3β or GSK3β and cdk5/p25 and more particularly of neurodegenerative diseases.

What is claimed is:

1. A compound of formula (I) or a salt thereof;

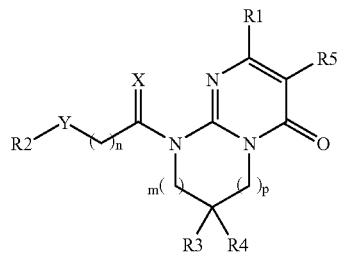

wherein:
X represents two hydrogen atoms, a sulfur atom, an oxygen atom or a C$_{1-2}$ alkyl group and a hydrogen atom;

Y represents a bond, an ethenylene group, an ethynylene group, an oxygen atom, a sulfur atom, a sulfonyl group, a sulfoxide group, a carbonyl group, a hydroxyiminomethylene group, a dioxolan group, a nitrogen atom being optionally substituted by a C$_{1-6}$ alkyl group, a phenyl group or a benzyl group; or a methylene group optionally substituted by one or two groups chosen from a C$_{1-6}$ alkyl group, a benzyl group, a hydroxyl group, a C$_{1-4}$ alkoxy group, a C$_{1-2}$ perhalogenated alkyl group, an amino group, an acetylamino group or a phenyl group;

R1 represents a 2, 3 or 4-pyridine ring optionally substituted by a C$_{3-6}$ cycloalkyl group, a C$_{1-4}$ alkyl group, a C$_{1-4}$ alkoxy group, a benzyl group or a halogen atom;

when Y represents a bond, a methylene group optionally substituted, a hydroxyiminomethylene group, a dioxolan group or a carbonyl group then R2 represents a $C_{1-6}$ alkyl group optionally substituted by a hydroxy group, a $C_{6,10}$ aryloxy or a $C_{6,10}$ arylamino group; a $C_{3-6}$ cycloalkyl group, a $C_{1-4}$ alkylthio group, a $C_{1-4}$ alkoxy group, a $C_{1-2}$ perhalogenated alkyl group, a $C_{1-3}$ halogenated alkyl group, a phenylthio group, a benzyl group, a benzene ring, an indan ring, a 5,6,7,8-tetrahydronaphthalene ring, a naphthalene ring, a pyridine ring, a pyrrole ring, a thiophene ring, a furan ring or an imidazole ring; the benzyl group or the rings being optionally substituted by 1 to 4 substituents selected from a $C_{1-6}$ alkyl group, a methylendioxy group, a halogen atom, a $C_{1-2}$ perhalogenated alkyl group, a $C_{1-3}$ halogenated alkyl group, a hydroxyl group, a $C_{1-4}$ alkoxy group, a nitro, a cyano, an amino, a $C_{1-5}$ monoalkylamino group, a $C_{2-10}$ dialkylamino group, a $C_{1-6}$ alkylcarbonylamino group, a $C_{6,10}$ arylcarbonylamino group, a $C_{1-4}$ alkylsulfonyl group, $C_{1-4}$ alkylsulfonyloxy group or a phenyl group;

when Y represents a ethenylene group, a ethynylene group, an oxygen atom, a sulfur atom, a sulfonyl group, a sulfoxide group or a nitrogen atom being optionally substituted then R2 represents a $C_{1-6}$ alkyl group optionally substituted by a hydroxy group, a $C_{6,10}$ aryloxy or a $C_{6,10}$ arylamino group; a $C_{3-6}$ cycloalkyl group, a $C_{1-2}$ perhalogenated alkyl group, a $C_{1-3}$ halogenated alkyl group, a benzyl group, a benzene ring, an indan ring, a 5,6,7,8-tetrahydronaphthalene ring, a naphthalene ring, a $C_{6,10}$ arylamino, a pyridine ring, a pyrrole ring, a thiophene ring, a furan ring or an imidazole ring ; the benzyl group or the rings being optionally substituted by 1 to 4 substituents selected from a $C_{1-6}$ alkyl group, a methylendioxy group, a halogen atom, a $C_{1-2}$ perhalogenated alkyl group, a $C_{1-3}$ halogenated alkyl group, a hydroxyl group, a $C_{1-4}$ alkoxy group, a nitro, a cyano, an amino, a $C_{1-5}$ monoalkylamino group, a $C_{2-10}$ dialkylamino group, a $C_{1-6}$ alkylcarbonylamino group, a $C_{6,10}$ arylcarbonylamino group, a $C_{1-4}$ alkylsulfonyl group, $C_{1-4}$ alkylsulfonyloxy group or a phenyl group;

R3 represents a hydrogen atom, a $C_{1-6}$ alkyl group, a hydroxy group, a $C_{1-4}$ alkoxy group or a halogen atom;

R4 represents a hydrogen atom, a $C_{1-6}$ alkyl group, a hydroxy group, a $C_{1-4}$ alkoxy group or a halogen atom;

R5 represents a hydrogen atom, a $C_{1-6}$ alkyl group or a halogen atom; with the proviso that when R3 and R4 represent each a hydrogen atom then R5 is not a hydrogen atom;

when m equals 0, p equals 1, 2 or 3, when m equals 1, p equals 0, 1 or 2, when m equals 2, p equals 0 or 1; and n represents 0 to 3.

2. The compound according to claim 1, wherein R1 represents an unsubstituted pyridine ring.

3. A pyrimidone derivative which is selected from the group consisting of:
9-[3-(2-Fluorophenyl)-propyl]-7,7-dimethyl-2-(pyridin-4-yl)-6,7,8,9-tetrahydro-4H-pyrimido[1,2-a]pyrimidin-4-one
9-(2-Oxo-2-phenyl-ethyl)-7,7-dimethyl-2-(pyridin-4-yl)-6,7,8,9-tetrahydro-4H-pyrimido[1,2-a]pyrimidin-4-one
9-(2-Hydroxy-2-phenyl-ethyl)-7,7-dimethyl-2-(pyridin-4-yl)-6,7,8,9-tetrahydro-4H-pyrimido[1,2-a]pyrimidin-4-one
9-(2-Oxo-2-phenyl-ethyl)-7,7-difluoro-2-(pyridin-4-yl)-6,7,8,9-tetrahydro-4H-pyrimido[1,2-a]pyrimidin-4-one
9-(2(S)-Hydroxy-2-phenyl-ethyl)-7,7-difluoro-2-(pyridin-4-yl)-6,7,8,9-tetrahydro-4H-pyrimido[1,2-a]pyrimidin-4-one
9-(2-Oxo-2-phenyl-ethyl)-3-fluoro-7,7-dimethyl-2-(pyridin-4-yl)-6,7,8,9-tetrahydro-4H-pyrimido[1,2-a]pyrimidin-4-one
9-[2-Oxo-2-(3-chlorophenyl)-ethyl]-7,7-dimethyl-2-(pyridin-4-yl)-6,7,8,9-tetrahydro-4H-pyrimido[1,2-a]pyrimidin-4-one
9-(2(S)-Hydroxy-2-phenyl-ethyl)-7,7-dimethyl-2-(pyridin-4-yl)-6,7,8,9-tetrahydro-4H-pyrimido[1,2-a]pyrimidin-4-one
9-[2-Oxo-2-(3-fluorophenyl)-ethyl]-7,7-dimethyl-2-(pyridin-4-yl)-6,7,8,9-tetrahydro-4H-pyrimido[1,2-a]pyrimidin-4-one
9-[2-Hydroxy-2-(3-chlorophenyl)-ethyl]-7,7-dimethyl-2-(pyridin-4-yl)-6,7,8,9-tetrahydro-4H-pyrimido[1,2-a]pyrimidin-4-one
9-[2-Hydroxy-2-(3-fluorophenyl)-ethyl]-7,7-dimethyl-2-(pyridin-4-yl)-6,7,8,9-tetrahydro-4H-pyrimido[1,2-a]pyrimidin-4-one
9-(2(S)-Hydroxy-2-phenyl-ethyl)-3-fluoro-7,7-dimethyl-2-(pyridin-4-yl)-6,7,8,9-tetrahydro-4H-pyrimido[1,2-a]pyrimidin-4-one
9-[2-Oxo-2-(4-fluorophenyl)-ethyl]-7,7-dimethyl-2-(pyridin-4-yl)-6,7,8,9-tetrahydro-4H-pyrimido[1,2-a]pyrimidin-4-one
9-[2-Oxo-2-(5,5,8,8-tetramethyl-5,6,7,8-tetrahydronaphth-2-yl)-ethyl]-7,7-dimethyl-2-(pyridin-4-yl)-6,7,8,9-tetrahydro-4H-pyrimido[1,2-a]pyrimidin-4-one
9-[2-Oxo-2-(3-methoxyphenyl)-ethyl]-7,7-dimethyl-2-(pyridin-4-yl)-6,7,8,9-tetrahydro-4H-pyrimido [1,2-a]pyrimidin-4-one
9-[2-Oxo-2-(4-phenylphenyl)-ethyl]-7,7-dimethyl-2-(pyridin-4-yl)-6,7,8,9-tetrahydro-4H-pyrimido[1,2-a]pyrimidin-4-one
9-[2-(1-Methyl-2-oxo-2-(3,4-methylendioxy-5-methoxyphenyl)-ethyl)]-7,7-dimethyl-2-(pyridin-4-yl)-6,7,8,9-tetrahydro-4H-pyrimido[1,2-a]pyrimidin-4-one
9-[2-Oxo-2-(4-chlorophenyl)ethyl]-7,7-dimethyl-2-(pyridin-4-yl)-6,7,8,9-tetrahydro-4H-pyrimido[1,2-a]pyrimidin-4-one
9-[2-Oxo-2-(naphth-2-yl)-ethyl]-7,7-dimethyl-2-(pyridin-4-yl)-6,7,8,9-tetrahydro-4H-pyrimido[1,2-a]pyrimidin-4-one
9-[2-Oxo-2-(4-methylphenyl)-ethyl]-7,7-dimethyl-2-(pyridin-4-yl)-6,7,8,9-tetrahydro-4H-pyrimido[1,2-a]pyrimidin-4-one
9-(2-Oxo-2-phenyl-ethyl)-7,7-dimethyl-3-bromo-2-(pyridin-4-yl)-6,7,8,9-tetrahydro-4H-pyrimido[1,2-a]pyrimidin-4-one
9-(2(S)-Methoxy-2-phenyl-ethyl)-7,7-dimethyl-2-(pyridin-4-yl)-6,7,8,9-tetrahydro-4H-pyrimido[1,2-a]pyrimidin-4-one
9-(3-Phenyl-propanoyl)-7,7-dimethyl-2-(pyridin-4-yl)-6,7,8,9-tetrahydro-4H-pyrimido[1,2-a]pyrimidin-4-one
9-(2-Hydroxy-2-methyl-2-phenyl-ethyl)-7,7-dimethyl-2-(pyridin-4-yl)-6,7,8,9-tetrahydro-4H-pyrimido[1,2-a]pyrimidin-4-one
9-(2-Methoxy-2-phenyl-2-trifluoromethyl-ethanoyl)-7,7-dimethyl-2-(pyridin-4-yl)-6,7,8,9-tetrahydro-4H-pyrimido[1,2-a]pyrimidin-4-one
9-(2-Hydroxy-2,2-diphenylethyl)-7,7-dimethyl-2-(pyridin-4-yl)-6,7,8,9-tetrahydro-4H-pyrimido[1,2-a]pyrimidin-4-one 9-(2-Hydroxyimino-2-phenyl-ethyl)-7,7-dimethyl-2-(pyridin-4-yl)-6,7,8,9-tetrahydro-4H-pyrimido[1,2-a]pyrimidin-4-one 9-(2-Hydroxy-2-methyl-2-phenyl-ethyl)-7,7-dimethyl-3-fluoro-2-(pyridin-4-yl)-6,7,8,9-tetrahydro-4H-pyrimido[1,2-a]pyrimidin-4-one 7,7-Dimethyl-9-(2-phenyl-[1,3]dioxolan-2-ylmethyl)-2-(pyridin-4-yl)-6,7,8,9-tetrahydro-4H-pyrimido [1,2-a]pyrimidin-4-one 9-(2,3-Dihydroxypropyl)-7,7-dimethyl-2-(pyridin-4-yl)-6,7,8,9-tetrahydro-4H-pyrimido[1,2-a]pyrimidin-4-one (2(R)-Methoxy-2-phenyl-ethyl)-7,7-dimethyl-2-(pyridin-4-yl)-6,7,8,9-tetrahydro-4H-pyrimido[1,2-a]pyrimidin-4-one 9-(2-Hydroxy-3-phenylaminopropyl)-7,7-dimethyl-2-(pyridin-4-yl)-6,7,8,9-tetrahydro-4H-pyrimido[1,2-a]pyrimidin-4-one 9-(2-Acetylamino-2-phenyl-ethyl)-7,7-dimethyl-2-(pyridin-4-yl)-6,7,8,9-tetrahydro-4H-pyrimido[1,2-a]pyrimidin-4-one 9-(2-Amino-2-phenyl-ethyl)-7,7-dimethyl-2-(pyridin-4-yl)-6,7,8,9-tetrahydro-4H-pyrimido[1,2-a]pyrimidin-4-one 9-(2-Hydroxy-3-phenoxypropyl)-7,7-dimethyl-2-(pyridin-4-yl)-6,7,8,9-tetrahydro-4H-pyrimido[1,2-a]pyrimidin-4-one 9-(2-Oxo-2-phenyl-ethyl)-3-fluoro-2-(pyridin-4-yl)-6,7,8,9-tetrahydro-4H-pyrimido[1,2-a]pyrimidin-4-one 9-[2-Oxo-2-(3-fluorophenyl)-ethyl]-3-fluoro-2-(pyridin-4-yl)-6,7,8,9-tetrahydro-4H-pyrimido[1,2-a]pyrimidin-4-one 9-(2-Oxo-2-phenyl-ethyl)-3-methyl-2-(pyridin-4-yl)-6,7,8,9-tetrahydro-4H-pyrimido[1,2-a]pyrimidin-4-one 9-(2-Oxo-2-phenyl-ethyl)-3-chloro-2-(pyridin-4-yl)-6,7,8,9-tetrahydro-4H-pyrimido[1,2-a]pyrimidin-4-one 9-(2-Oxo-2-phenyl-ethyl)-3-bromo-2-(pyridin-4-yl)-6,7,8,9-tetrahydro-4H-pyrimido[1,2-a]pyrimidin-4-one 2-(7-Methyl-6-oxo-8-pyridinyl-3,4-dihydro-2H, 6H pyrimido[1,2-a]pyrimidin-1-yl)-N-phenyl-acetamide 9-(2(S)-Hydroxy-2-phenyl-ethyl)-3-chloro-2-(pyridin-4-yl)-6,7,8,9-tetrahydro-4H-pyrimido[1,2-a]pyrimidin-4-one 9-(2(S)-Hydroxy-2-phenyl-ethyl)-3-methyl-2-(pyridin-4-yl)-6,7,8,9-tetrahydro-4H-pyrimido[1,2-a]pyrimidin-4-one 9-(2(S)-Hydroxy-2-phenyl-ethyl)-3-fluoro-2-(pyridin-4-yl)-6,7,8,9-tetrahydro-4H-pyrimido[1,2-a]pyrimidin-4-one 9-(2(S)-Methoxy-2-phenyl-ethyl)-3-fluoro-2-(pyridin-4-yl)-6,7,8,9-tetrahydro-4H-pyrimido[1,2-a]pyrimidin-4-one 9-(2(R)-Methoxy-2-phenyl-ethyl)-3-fluoro-2-(pyridin-4-yl)-6,7,8,9-tetrahydro-4H-pyrimido[1,2-a]pyrimidin-4-one 9-[3-(2-Fluorophenyl)propyl]-7-hydroxy-2-(pyridin-4-yl)-6,7,8,9-tetrahydro 4H-pyrimido[1,2-a]pyrimidin-4-one 9-[3-(2-Fluorophenyl)propyl]-7-methoxy-2-(pyridin-4-yl)-6,7,8,9-tetrahydro-4H-pyrimido[1,2-a]pyrimidin-4-one 9-(2-Oxo-2-phenyl-ethyl)-7-methyl-2-(pyridin-4-yl)-6,7,8,9-tetrahydro 4H-pyrimido[1,2-a]pyrimidin-4-one 9-(2-Hydroxy-2-phenyl-ethyl)-7-methyl-2-(pyridin-4-yl)-6,7,8,9-tetrahydro-4H-pyrimido[1,2-a]pyrimidin-4-one 9-(2-Hydroxy-2-methyl-2-phenyl-ethyl)-7,7-dimethyl-2-(pyridin-4-yl)-6,7,8,9-tetrahydro-4H-pyrimido[1,2-a]pyrimidin-4-one 9-(2-Hydroxy-2-methyl-2-phenyl-ethyl)-7,7-dimethyl-2-(pyridin-4-yl)-6,7,8,9-tetrahydro-4H-pyrimido[1,2-a]pyrimidin-4-one 9-(2(R)-Methoxy-2-phenyl-ethyl)-7,7-dimethyl-2-(pyridin-4-yl)-6,7,8,9-tetrahydro-4H-pyrimido[1,2-a]pyrimidin-4-one 3-Fluoro-9-[2-(4-fluoro-2-methoxy-phenyl)-ethyl]-2-(pyridin-4-yl)-6,7,8,9-tetrahydro-4H-pyrimido[1,2-a]pyrimidin-4-one 9-Indan-2-ylmethyl-7,7-dimethyl-2-(pyridin-4-yl)-6,7,8,9-tetrahydro-4H-pyrimido[1,2-a]pyrimidin-4-one 3-Fluoro-9-[2-(4-fluoro-2-methoxy-phenyl)-ethyl]-7,7-dimethyl-2-(pyridin-4-yl)-6,7,8,9-tetrahydro-4H-pyrimido[1,2-a]pyrimidin-4-one; and 9-[2-(4-Fluoro-2-methoxy-phenyl)-ethyl]-7,7-dimethyl-2-(pyridin-4-yl)-6,7,8,9-tetrahydro-4H-pyrimido[1,2-a]pyrimidin-4-one;

or a salt thereof.

4. A pyrimidone derivative which is selected from the group consisting of:

[3-(2-Fluoro-phenyl)-propyl]-2,2-dimethyl-7-(pyridin-4-yl)-2,3-dihydro-1H-imidazo[1,2-a]pyrimidin-5-one

[2-Oxo-2-phenylethyl]-2,2-dimethyl-7-(pyridin-4-yl)-2,3-dihydro-1H-imidazo[1,2-a]pyrimidin-5-one

[2-Hydroxy-2-phenylethyl]-2,2-dimethyl-7-(pyridin-4-yl)-2,3-dihydro-1H-imidazo[1,2-a]pyrimidin-5-one

[2-Oxo-2-(4-chlorophenyl)ethyl]-2,2-dimethyl-7-(pyridin-4-yl)-2,3-dihydro-1H-imidazo[1,2-a]pyrimidin-5-one

[2-Oxo-2-(4-methylphenyl)ethyl]-2,2-dimethyl-7-(pyridin-4-yl)-2,3-dihydro-1H-imidazo[1,2-a]pyrimidin-5-one

[2-Oxo-4-phenylphenyl]-2,2-dimethyl-7-(pyridin-4-yl)-2,3-dihydro-1H-imidazo[1,2-a]pyrimidin-5-one

[1-Methyl-2-oxo-2-(3,4-methylendioxy-5-methoxyphenyl)-ethyl]-2,2-dimethyl-7-(pyridin-4-yl)-2,3-dihydro-1H-imidazo[1,2-a]pyrimidin-5-one

[2-Oxo-2-(naphth-2-yl)-ethyl]-2,2-dimethyl-7-(pyridin-4-yl)-2,3-dihydro-1H-imidazo[1,2-a]pyrimidin-5-one

[2-Oxo-2-(4-fluorophenyl)-ethyl]-2,2-dimethyl-7-(pyridin-4-yl)-2,3-dihydro-1H-imidazo[1,2-a]pyrimidin-5-one

[2-Oxo-2-(3-methoxyphenyl)-ethyl]-2,2-dimethyl-7-(pyridin-4-yl)-2,3-dihydro-1H-imidazo[1,2-a]pyrimidin-5-one; and

[2-Oxo-2-(5,5,8,8-tetramethyl-5,6,7,8-tetrahydronaphth-2-yl)-ethyl]-2,2-dimethyl-7-(pyridin-4-yl)-2,3-dihydro-1H-imidazo[1,2-a]pyrimidin-5-one;

or a salt thereof.

5. A pyrimidone derivative which is selected from the group consisting of:

9-[2-(4-Fluoro-2-methoxy-phenyl)-ethyl]-8-methyl-2-(pyridin-4-yl)-6,7,8,9-tetrahydro-pyrimido[1,2-a]pyrimidin-4-one 9-[2-(4-Fluoro-2-methoxy-phenyl)-ethyl]-8,8-dimethyl-2-(pyridin-4-yl)-6,7,8,9-tetrahydro-pyrimido[1,2-a]pyrimidin-4-one 9-[2-(4-Fluoro-phenyl)-ethyl]-8-methyl-2-(pyridin-4-yl)-6,7,8,9-tetrahydro-pyrimido[1,2-a]pyrimidin-4-one 8-Methyl-9-(2-oxo-2-phenyl-ethyl)-2-(pyridin-4-yl)-6,7,8,9-tetrahydro-pyrimido[1,2-a]pyrimidin-4-one 9-[2-(2,5-Dimethoxy-phenyl)-ethyl]-8-methyl-2-(pyridin-4-yl)-6,7,8,9-tetrahydro-pyrimido[1,2-a]pyrimidin-4-one 9-[2-(2-methoxy-phenyl)-ethyl]-8-methyl-2-(pyridin-4-yl)-6,7,8,9-tetrahydro-pyrimido[1,2-a]pyrimidin-4-one.

9-[2(S)-Hydroxy-2-phenyl-ethyl]-8-methyl-2-(pyridin-4-yl)-6,7,8,9-tetrahydro-pyrimido[1,2-a]pyrimidin-4-one 9-[2(S)-Hydroxy-2-phenyl-ethyl]-8,8-dimethyl-2-(pyridin-4-yl)-6,7,8,9-tetrahydro-pyrimido[1,2-a]pyrimidin-4-one
8-Methyl-9-[naphthalen-1-ylmethyl]-2-(pyridin-4-yl)-6,7,8,9-tetrahydro-pyrimido[1,2-a]pyrimidin-4-one
8,8-Dimethyl-9-[2-oxo-2-phenyl-ethyl]-2(pyridin-4-yl)-6,7,8,9-tetrahydro-pyrimido[1,2-a]pyrimidin-4-one
8-Methyl-9-[naphthalen-2-ylmethyl]-2-(pyridin-4-yl)-6,7,8,9-tetrahydro-pyrimido[1,2-a]pyrimidin-4-one
9-[2-(3-Methoxy-phenyl)-2-oxo-ethyl]-8-methyl-2-(pyridin-4-yl)-6,7,8,9-tetrahydro-pyrimido[1,2-a]pyrimidin-4-one
9-[2-(3-Chloro-phenyl)-2-oxo-ethyl]-8-methyl-2-(pyridin-4-yl)-6,7,8,9-tetrahydro-pyrimido[1,2-a]pyrimidin-4-one
8,8-Dimethyl-9-[2(S)-phenyl-propyl]-2-(pyridin-4-yl)-6,7,8,9-tetrahydro-pyrimido[1,2-a]pyrimidin-4-one
8,8-Dimethyl-9-[2(R)-phenyl-propyl]-2-(pyridin-4-yl)-6,7,8,9-tetrahydro-pyrimido[1,2-a]pyrimidin-4-one
8-Ethyl-9-[2-oxo-2-phenyl-ethyl]-2-(pyridin-4-yl)-6,7,8,9-tetrahydro-pyrimido[1,2-a]pyrimidin-4-one
8-Ethyl-9-[2(S)-hydroxy-2-phenyl-ethyl]-2-(pyridin-4-yl)-6,7,8,9-tetrahydro-pyrimido[1,2-a]pyrimidin-4-one
3-Fluoro-8-methyl-9-(2-oxo-2-phenyl-ethyl)-2-(pyridin-4-yl)-6,7,8,9-tetrahydro-pyrimido[1,2-a]pyrimidin-4-one
8,8-Dimethyl-9[naphthalen-1-ylmethyl]-2-(pyridin-4-yl)-6,7,8,9-tetrahydro-pyrimido[1,2-a]pyrimidin-4-one
9-[2-(4-Fluoro-phenyl)-2(S)-hydroxy-ethyl]-8,8-dimethyl-2-(pyridin-4-yl)-6,7,8,9-tetrahydro-pyrimido[1,2-a]pyrimidin-4-one
9-[2-(3-Fluoro-phenyl)-2-hydroxy-ethyl]-8-methyl-2-(pyridin-4-yl)-6,7,8,9-tetrahydro-pyrimido[1,2-a]pyrimidin-4-one
9-[2-(3,5-Dichloro-phenyl)-2-hydroxy-ethyl]-8-methyl-2-(pyridin-4-yl)-6,7,8,9-tetrahydro-pyrimido[1,2-a]pyrimidin-4-one
9-[2-Benzo[1,3]dioxol-5-yl-2-oxo-ethyl]-8-methyl-2-(pyridin-4-yl)-6,7,8,9-tetrahydro-pyrimido[1,2-a]pyrimidin-4-one
9-[2-(3-Bromo-phenyl)-2(S)-hydroxy-ethyl]-8,8-dimethyl-2-(pyridin-4-yl)-6,7,8,9-tetrahydro-pyrimido[1,2-a]pyrimidin-4-one
9-[2-(2,3-Dihydro-benzo[1,4]dioxin-6-yl)-2-oxo-ethyl]-8-methyl-2-(pyridin-4-yl)-6,7,8,9-tetrahydro-pyrimido[1,2-a]pyrimidin-4-one
3-Fluoro-9-(2-(S)-hydroxy-2-phenyl-ethyl)-8-methyl-2-(pyridin-4-yl)-6,7,8,9-tetrahydro-pyrimido[1,2-a]pyrimidin-4-one
9-(2-Biphenyl-4-yl-2(S)-hydroxy-ethyl)-8,8-dimethyl-2-(pyridin-4-yl)-6,7,8,9-tetrahydro-pyrimido[1,2-a]pyrimidin-4-one
9-[2-(3-Fluoro-phenyl)-2(S)-hydroxy-ethyl]-8,8-dimethyl-2-(pyridin-4-yl)-6,7,8,9-tetrahydro-pyrimido[1,2-a]pyrimidin-4-one
9-(2(S)-Hydroxy-2-naphthalen-2-yl-ethyl)-8,8-dimethyl-2-(pyridin-4-yl)-6,7,8,9-tetrahydro-pyrimido[1,2-a]pyrimidin-4-one
9-[2-(4-Chloro-phenyl)-2(S)-hydroxy-ethyl]-8,8-dimethyl-2-(pyridin-4-yl)-6,7,8,9-tetrahydro-pyrimido[1,2-a]pyrimidin-4-one
9-[2-(3,4-Dichlorophenyl)-2(S)-hydroxy-ethyl]-8,8-dimethyl-2-(pyridin-4-yl)-6,7,8,9-tetrahydro-pyrimido[1,2-a]pyrimidin-4-one
9-(2(S)-Hydroxy-2-p-tolyl-ethyl)-8,8-dimethyl-2-(pyridin-4-yl)-6,7,8,9-tetrahydro-pyrimido[1,2-a]pyrimidin-4-one
3-Bromo-8-methyl-9-(2-oxo-2-phenyl-ethyl)-2-pyridin-4-yl-6,7,8,9-tetrahydro-pyrimido[1,2-a]pyrimidin-4-one
9-[2(S)-Hydroxy-2-(3-methoxy-phenyl)-ethyl]-8,8-dimethyl-2-(pyridin-4-yl)-6,7,8,9-tetrahydro-pyrimido[1,2-a]pyrimidin-4-one
9-[2-(2,4-Dichloro-phenyl)-2(S)-hydroxy-ethyl]-8,8-dimethyl-2-(pyridin-4-yl)-6,7,8,9-tetrahydro-pyrimido[1,2-a]pyrimidin-4-one
3-Fluoro-9-(2(S)-hydroxy-2-phenyl-ethyl)-8,8-dimethyl-2-(pyridin-4-yl)-6,7,8,9-tetrahydro-pyrimido[1,2-a]pyrimidin-4-one;
9-[2-(3-Methoxy-phenyl)-2-oxo-ethyl]-8,8-dimethyl-2-pyridin-4-yl-6,7,8,9-tetrahydro-pyrimido[1,2-a]pyrimidin-4-one;
9-[2(S)-Hydroxy-2-phenyl-ethyl]-8-methyl-2-(pyridin-4-yl)-6,7,8,9-tetrahydro-pyrimido[1,2-a]pyrimidin-4-one (diastereoisomer I);
9-[2(S)-Hydroxy-2-phenyl-ethyl]-8-methyl-2-(pyridin-4-yl)-6,7,8,9-tetrahydro-pyrimido[1,2-a]pyrimidin-4-one (diastereoisomer II);
8,8-dimethyl 9-(2-oxo-2-p-tolyl-ethyl)-ethyl)-2-pyridin-4-yl-6,7,8,9-tetrahydro-pyrimido[1,2-a]pyrimidin-4-one;
9-[2-(3-Bromo-phenyl)-2-oxo-ethyl]-8,8-dimethyl-2-pyridin-4-yl-6,7,8,9-tetrahydro-pyrimido[1,2-a]pyrimidin-4-one;
4-[2-(2,2-Dimethyl-6-oxo-8-pyridin-4-yl-3,4-dihydro-2H,6H-pyrimido[1,2-a]pyrimidin-1-yl)-1-hydroxy-ethyl]-benzonitrile;
9-[2-(3-Fluoro-phenyl)-2-oxo-ethyl]-8,8-dimethyl-2-pyridin-4-yl-6,7,8,9-tetrahydro-pyrimido[1,2-a]pyrimidin-4-one;
9-[2-(3,4-Dichloro-phenyl)-2-hydroxy-ethyl]-8,8-dimethyl-2-pyridin-4-yl-6,7,8,9-tetrahydro-pyrimido[1,2-a]pyrimidin-4-one;
9-[2-(4-Chloro-phenyl)-2-hydroxy-ethyl]-8-ethyl-2-pyridin-4-yl-6,7,8,9-tetrahydro-pyrimido[1,2-a]pyrimidin-4-one;
9-[2-(3-Bromo-phenyl)-2-oxo-ethyl]-8-ethyl-2-pyridin-4-yl-6,7,8,9-tetrahydro-pyrimido[1,2-a]pyrimidin-4-one;
9-[2-(4-chloro-phenyl)-2-oxo-ethyl]-8-ethyl-2-pyridin-4-yl-6,7,8,9-tetrahydro-pyrimido[1,2-a]pyrimidin-4-one; and
8-Ethyl-9-(2-hydroxy-2-p-tolyl-ethyl)-2-pyridin-4-yl-6,7,8,9-tetrahydro-pyrimido[1,2-α]pyrimidin-4-one
or a salt thereof.

6. A method for treatment non-insulin dependent diabetes; which comprises administering to a patient in need of said treatment an effective amount of a compound according to claim 1.

7. A method for treatment of non-insulin dependent diabetes; which comprises administering to a patient in need of said treatment an effective amount of a compound according to claim 2.

8. A method for treatment of non-insulin dependent diabetes; which comprises administering to a patient in need of said treatment an effective amount of a compound according to claim 3.

9. A method for treatment of non-insulin dependent diabetes; which comprises administering to a patient in need of said treatment an effective amount of a compound according to claim 4.

10. A method for treatment of non-insulin dependent diabetes; which comprises administering to a patient in need of said treatment an effective amount of a compound according to claim 5.

* * * * *